(12) United States Patent
Shu

(10) Patent No.: US 7,578,843 B2
(45) Date of Patent: Aug. 25, 2009

(54) HEART VALVE PROSTHESIS

(75) Inventor: Mark C. S. Shu, Rancho Santa Margarita, CA (US)

(73) Assignee: Medtronic, Inc., Minneapolis, MN (US)

( * ) Notice: Subject to any disclaimer, the term of this patent is extended or adjusted under 35 U.S.C. 154(b) by 418 days.

(21) Appl. No.: 10/404,233

(22) Filed: Apr. 1, 2003

(65) Prior Publication Data

US 2004/0030381 A1 Feb. 12, 2004

Related U.S. Application Data

(63) Continuation-in-part of application No. 10/196,527, filed on Jul. 16, 2002, now Pat. No. 7,172,625.

(51) Int. Cl.
*A61F 2/24* (2006.01)
(52) U.S. Cl. .................................................. 623/2.11
(58) Field of Classification Search ......... 623/2.1–2.35, 623/2.36–2.42
See application file for complete search history.

(56) References Cited

U.S. PATENT DOCUMENTS

| 3,143,742 A | 8/1964 | Cromie |
| 3,997,923 A | 12/1976 | Possis ............................ 3/1.5 |

(Continued)

FOREIGN PATENT DOCUMENTS

EP 1057460 12/2000

(Continued)

OTHER PUBLICATIONS

Artif. Organs, vol. 16 No. 3.1992 pp. 294-297 Detachable Shape-Memory Sewing Ring For Heart Valves by: Josef Jansen, Sebastian Willeke, Helmut Reul, and Gunter Rau from Helmholtz Institute for Biomedical Engineering, Technical University of Aachen, Aachen, Germany.

(Continued)

*Primary Examiner*—Alvin J Stewart
(74) *Attorney, Agent, or Firm*—Mike Jaro; Jeffrey J. Hohenshell

(57) ABSTRACT

A heart valve prosthesis has a frame that includes at least one outwardly extending annular flange adjacent to a suturing ring and a band comprising an inwardly extending annular flange that is capable of engagement with the annular flange of the frame. A tortuous path is formed between the annular flange of the frame and the annular flange of the band that can engage and restrain a suture placed between them. One or more split portions or tab portions on the band are adapted to lock the band in engagement with the flange of the frame. Such a device can be used to more easily replace a heart valve by advancing a sutures through a suturing ring on the valve and the valvular rim such that they are brought outward of the flange extending from the frame and then advancing the band over the valve and over the sutures at a proximal, outflow end of the valve until the band engages the flange and captures the sutures between the band and the flange.

22 Claims, 22 Drawing Sheets

U.S. PATENT DOCUMENTS

| | | | |
|---|---|---|---|
| 4,078,268 A | 3/1978 | Possis | 3/1.5 |
| RE31,040 E | 9/1982 | Possis | 3/1.5 |
| 4,364,126 A | 12/1982 | Rosen et al. | |
| 4,506,394 A * | 3/1985 | Bedard | 623/2.38 |
| 4,535,483 A * | 8/1985 | Klawitter et al. | 623/2.4 |
| 4,680,031 A | 7/1987 | Alonso | 623/2 |
| 4,705,516 A | 11/1987 | Barone et al. | 623/2 |
| 4,790,843 A | 12/1988 | Carpentier et al. | 623/2 |
| 4,892,541 A | 1/1990 | Alonso | 623/2 |
| 5,032,128 A | 7/1991 | Alonso | 623/2 |
| 5,035,709 A * | 7/1991 | Wieting et al. | 623/2.2 |
| 5,071,431 A * | 12/1991 | Sauter et al. | 623/2.4 |
| 5,104,406 A * | 4/1992 | Curcio et al. | 623/2.39 |
| 5,332,402 A | 7/1994 | Teitelbaum | |
| 5,397,346 A | 3/1995 | Walker et al. | 623/2 |
| 5,397,348 A * | 3/1995 | Campbell et al. | 623/2.38 |
| 5,562,729 A * | 10/1996 | Purdy et al. | 623/2.19 |
| 5,776,188 A | 7/1998 | Shepherd et al. | |
| 5,843,179 A | 12/1998 | Vanney et al. | |
| 5,855,603 A | 1/1999 | Reif | 623/2 |
| 5,876,436 A | 3/1999 | Vanney et al. | 623/2 |
| 5,976,183 A * | 11/1999 | Ritz | 623/2.11 |
| 5,984,959 A | 11/1999 | Robertson et al. | |
| 6,007,577 A * | 12/1999 | Vanney et al. | 623/2.31 |
| 6,042,607 A | 3/2000 | Williamson, IV et al. | |
| 6,074,418 A | 6/2000 | Buchanan et al. | |
| 6,106,550 A | 8/2000 | Magovern et al. | 623/2.38 |
| 6,113,632 A * | 9/2000 | Reif | 623/2.4 |
| 6,139,575 A | 10/2000 | Shu et al. | 623/2.12 |
| 6,143,024 A | 11/2000 | Campbell et al. | |
| 6,143,025 A * | 11/2000 | Stobie et al. | 623/2.39 |
| 6,162,233 A | 12/2000 | Williamson, IV et al. | |
| 6,176,877 B1 | 1/2001 | Buchanan et al. | 623/2.39 |
| 6,197,054 B1 * | 3/2001 | Hamblin et al. | 623/2.38 |
| 6,217,611 B1 | 4/2001 | Klostermeyer | 623/2.38 |
| 6,241,765 B1 | 6/2001 | Griffin et al. | |
| 6,287,339 B1 | 9/2001 | Vazquez et al. | |
| 6,299,638 B1 * | 10/2001 | Sauter | 623/1.26 |
| 6,358,278 B1 * | 3/2002 | Brendzel et al. | 623/2.39 |
| 6,402,780 B2 | 6/2002 | Williamson, IV et al. | |
| 6,419,696 B1 | 7/2002 | Ortiz et al. | |
| 6,530,952 B2 | 3/2003 | Vesely | |
| 6,569,196 B1 | 5/2003 | Vesely | |
| 6,602,289 B1 | 8/2003 | Colvin et al. | |
| 6,692,513 B2 | 2/2004 | Streeter et al. | |
| 6,709,457 B1 * | 3/2004 | Otte et al. | 623/2.4 |
| 6,716,243 B1 | 4/2004 | Colvin et al. | |
| 6,733,525 B2 | 5/2004 | Yang et al. | |
| 6,764,508 B1 | 7/2004 | Roehe et al. | |
| 6,769,434 B2 | 8/2004 | Liddicoat et al. | |
| 6,786,924 B2 | 9/2004 | Ryan et al. | |
| 6,790,229 B1 | 9/2004 | Berreklouw | |
| 6,846,325 B2 | 1/2005 | Liddicoat | |
| 6,893,459 B1 | 5/2005 | Macoviak | |
| 6,896,690 B1 | 5/2005 | Lambrecht et al. | |
| 6,929,653 B2 | 8/2005 | Streeter | |
| 6,939,365 B1 | 9/2005 | Fogarty et al. | |
| 6,945,997 B2 | 9/2005 | Van Le Huynh et al. | |
| 7,011,681 B2 | 3/2006 | Vesely | |
| 7,025,780 B2 | 4/2006 | Gabbay | |
| 7,097,659 B2 | 8/2006 | Woolfson et al. | |
| 7,172,625 B2 | 2/2007 | Shu | |
| 7,201,761 B2 | 4/2007 | Woolfson et al. | |
| 7,300,463 B2 | 11/2007 | Liddicoat | |
| 2002/0058994 A1 | 5/2002 | Hill et al. | 623/2.11 |
| 2002/0151970 A1 | 10/2002 | Garrison et al. | |
| 2003/0023302 A1 | 1/2003 | Moe et al. | 623/2.4 |
| 2003/0036791 A1 | 2/2003 | Philipp et al. | |
| 2003/0109924 A1 | 6/2003 | Cribier | |
| 2003/0199963 A1 | 10/2003 | Tower et al. | |
| 2003/0199971 A1 | 10/2003 | Tower et al. | |
| 2004/0015232 A1 | 1/2004 | Shu | |
| 2004/0030381 A1 | 2/2004 | Shu | |
| 2004/0122514 A1 | 6/2004 | Fogarty et al. | |
| 2004/0122516 A1 | 6/2004 | Fogarty et al. | |
| 2004/0210305 A1 | 10/2004 | Shu | |
| 2005/0010285 A1 | 1/2005 | Lambrecht et al. | |
| 2005/0033398 A1 | 2/2005 | Seguin | |
| 2005/0043760 A1 | 2/2005 | Fogarty et al. | |
| 2005/0165479 A1 | 7/2005 | Drews et al. | |
| 2005/0234546 A1 | 10/2005 | Nugent et al. | |
| 2005/0240263 A1 | 10/2005 | Fogarty et al. | |
| 2005/0251252 A1 | 11/2005 | Stobie | |
| 2005/0283231 A1 | 12/2005 | Haug et al. | |
| 2006/0052867 A1 | 3/2006 | Revuelta et al. | |
| 2006/0095125 A1 | 5/2006 | Chinn et al. | |
| 2006/0195184 A1 | 8/2006 | Lane et al. | |
| 2006/0271175 A1 | 11/2006 | Woolfson et al. | |

FOREIGN PATENT DOCUMENTS

| | | |
|---|---|---|
| EP | 171 059 B1 | 2/2005 |
| GB | 1093599 | 12/1967 |
| GB | 2011259 | 7/1979 |
| WO | 2004/089246 | 10/2004 |

OTHER PUBLICATIONS

Lutter et al, Percutaneous Valve Replacement: Current State and Future Prospects; Ann Thorac Surg 2004;78:2199-2206
USPTO Final Office Action for U.S. Appl. No. 10/792,186, mailed Nov. 16, 2007 (7 pgs.).

* cited by examiner

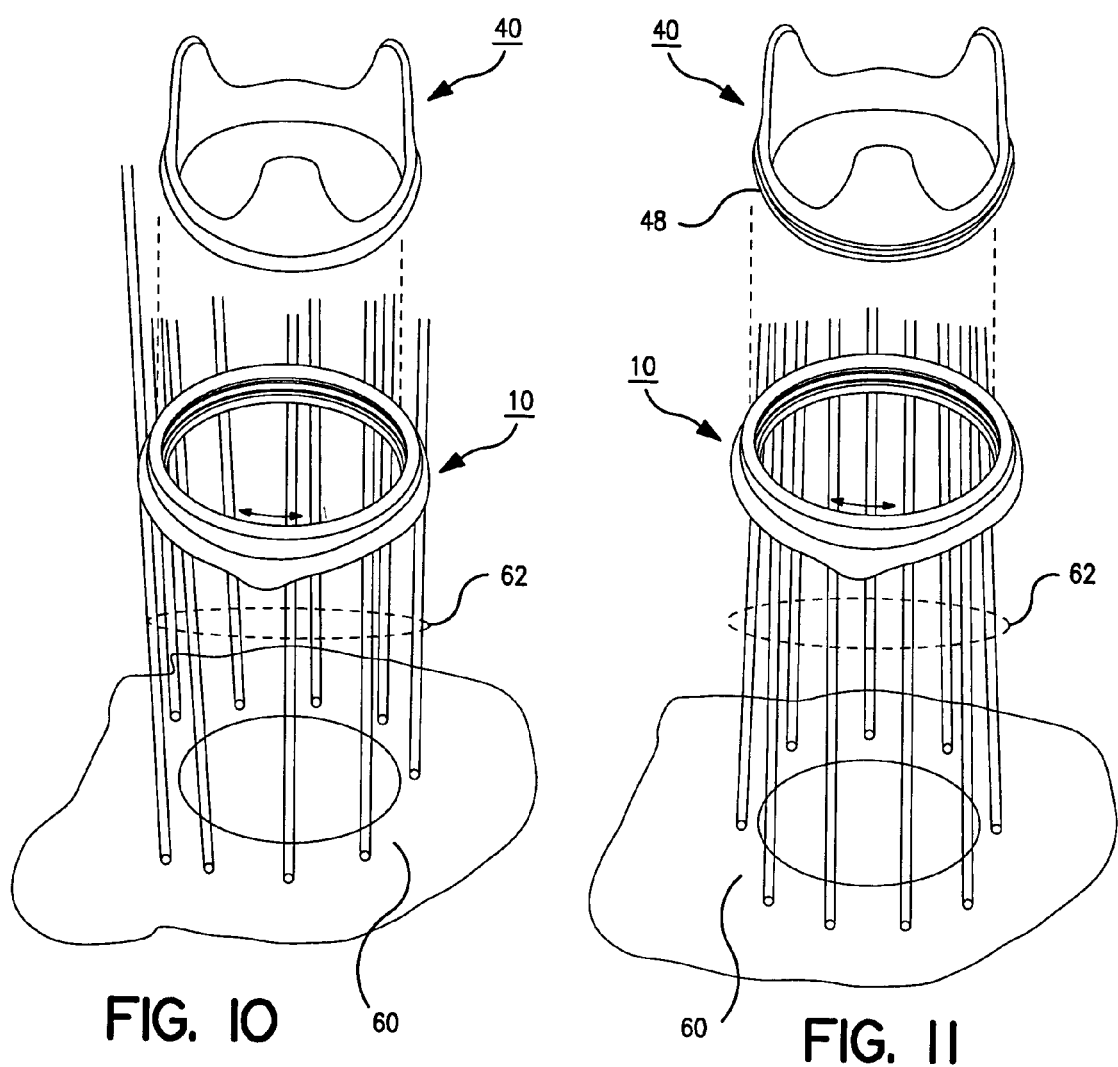

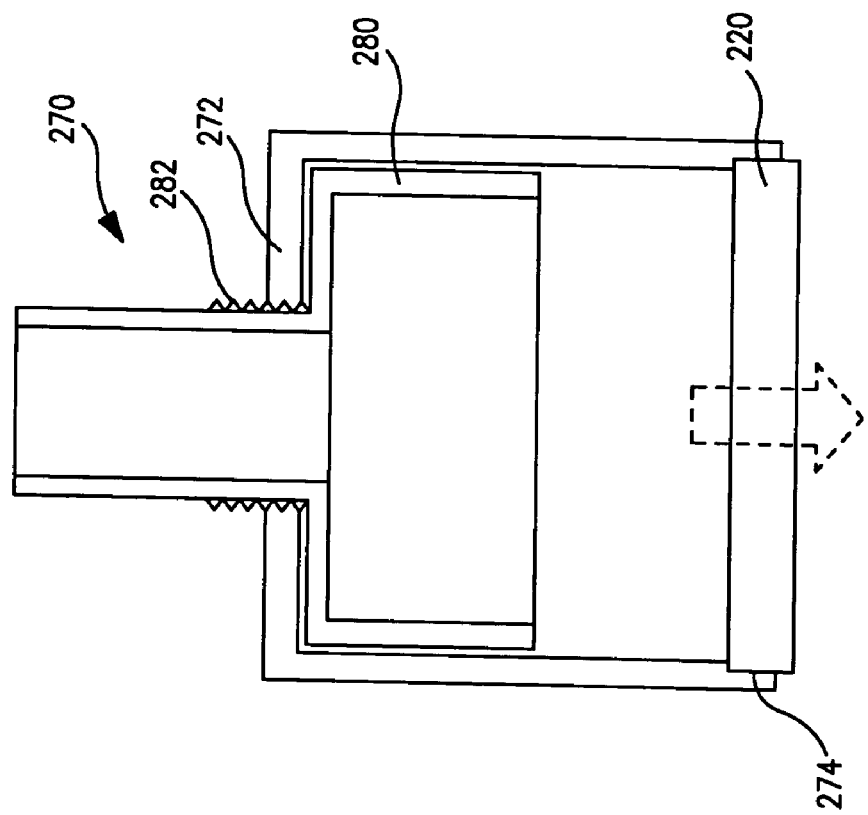
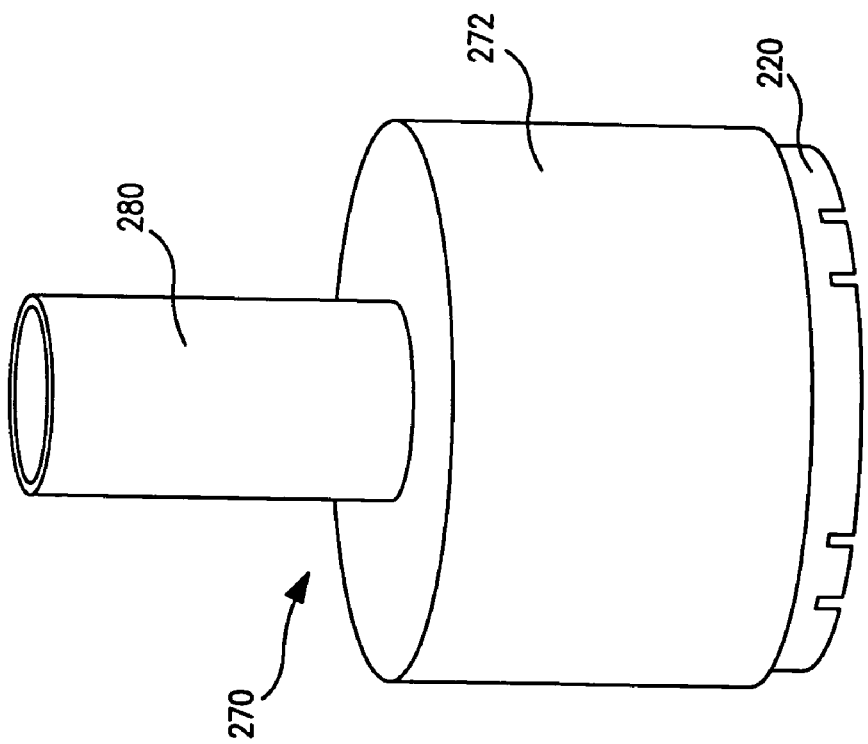

HEART VALVE PROSTHESIS

This application is a continuation-in-part of Ser. No. 10/196,527 filed Jul. 16, 2002 now U.S. Pat. No. 7,172,625, which is incorporated by reference herein in its entirety.

FIELD OF THE INVENTION

This invention relates generally to implantable heart valve prostheses, particularly to improvements in a heart valve prosthesis facilitating initial implantation of the suturing ring and replacement of a chronically implanted heart valve mechanism supported by the suturing ring providing enhanced durability reliability, ease of use, and ease of manufacture.

BACKGROUND OF THE INVENTION

Implantable heart valve prostheses have been used to replace various diseased or damaged natural aortic valves, mitral valves, pulmonic valves and tricuspid valves of the heart. The aortic and mitral valves are most frequently replaced due to heart disease, congenital defects or injury. The mitral valve controls the flow of blood between the left atrium and the left ventricle and the aortic valve controls the blood flow from the left ventricle into the aorta. Generally, the known heart valve prostheses are either bioprostheses or mechanical heart valve prostheses.

The bioprostheses or "tissue valves" are generally made of a suitable animal tissue, e.g., harvested swine valve leaflets, mounted onto a stationary metal or plastic frame, referred to as a "stent". Exemplary tissue valves formed of swine valve leaflets mounted to struts of a stent are those disclosed in U.S. Pat. Nos. 4,680,031, 4,892,541, and 5,032,128 as well as the MEDTRONIC® Hancock II® and Mosaic® stented tissue valves. Some prosthetic tissue valves are formed from treated integral swine valve leaflets and valve annulus structure, e.g. the MEDTRONIC® Freestyle® stentless aortic root bioprostheses Modern mechanical heart valve prostheses are typically formed of an annular valve seat in a relatively rigid valve body and one or more occluding disk or pair of leaflets that is movable between a closed, seated position in the annular valve seat and an open position in a prescribed range of motion. Such mechanical heart valves are formed of blood compatible, non-thrombogenic materials, typically currently comprising pyrolytic carbon and titanium. Hinge mechanisms and/or pivoting guides entrap and prescribe the range of motion of the disk or leaflets between open and closed positions. Exemplary bi-leaflet mechanical heart valves are disclosed in commonly assigned U.S. Pat. Nos. 4,935,030 and 6,139,575 and in U.S. Pat. Nos. 6,176,877 and 6,217,611.

Mechanical and tissue valves have advantages and disadvantages. By their very nature, mechanical heart valves have metal or plastic surfaces exposed to the blood flow, which remain thrombogenic even long time after their implantation by major surgery. The opening and closing of mechanical heart valve occluders can damage blood elements and trigger a coagulent cascade. Blood flow disturbances in certain mechanical valves are also believed to aggravate blood coagulation. Therefore, patients having such mechanical heart valves can avoid potentially life threatening embolus formation only by taking anti-thrombogenic or anti-coagulent medication on a regular basis. Porcine tissue valves include three cusps or leaflets of a heart valve excised from pigs and preserved by treatment with glutaraldehyde. The preserved porcine tissue is thrombogenic, and therefore, the human patient takes anti-thrombogenic or anti-coagulent medication at least a period of time after the surgical implantation of a tissue valve. Valve leaflet opening and closing characteristics and blood flow past open tissue leaflets of tissue valves can be superior to those afforded by mechanical valves. However, tissue leaflets can become calcified over time distorting the leaflet shape and ultimately leading to failure of the tissue leaflets to fully close or open. Proposals have been advanced to form mechanical heart valve prostheses from flexible, anti-thrombogenic, polymeric sheets or fabrics that are resistant to calcification mounted to stents to function like stented tissue valves also been proposed as exemplified by U.S. Pat. No. 5,562,729. However, calcification and tear issues of polymeric materials remain to be solved before a polymeric valve can be realized.)

Such mechanical and tissue valve prostheses are intended to be sutured to peripheral tissue of a natural heart valve orifice (the "valvar rim") after surgical removal of damaged or diseased natural valve structure. Modern prosthetic heart valves are typically supplied with a sewing or suturing ring surrounding the valve body or stent that is to be sutured by the surgeon to the valvar rim. Suturing rings typically comprise a fabric strip made of synthetic fiber that is biologically inert and does not deteriorate over time in the body, such as polytetrafluoroethylene (e.g., "Teflon PTFE") or polyester (e.g., "Dacron"), that is woven having interstices permeable to tissue ingrowth. The valve body or stent is typically circular or ring shaped having an outer surface or sidewall shaped to fit with an inner sidewall of the suturing ring. In some cases, the suturing ring fabric is shaped to extend outward to provide a flattened collar or skirt that can be applied against and sutured to the valvar rim, as shown for example in U.S. Pat. No. 3,997,923.

It is proposed in the prior art to make the valve body or stent rotatable within the annulus of the suturing ring. The surgeon can first suture the suturing ring to the valvar rim and then rotate the valve body or stent within the annulus of the suturing ring in order to adjust the angular orientation of the valve mechanism in the path of blood flow. In this way, the valve mechanism can be rotated to minimize interference with the adjacent heart structure or to divert blood flow past the open valve leaflet(s) in an optimal flow direction. Such rotation of the valve mechanism with respect to and within the annulus of the suturing ring requires a rotational torque sufficiently small as to avoid damage to the sutured valvar rim or loosening of the sutures, and yet sufficiently great so that the valve mechanism, when properly positioned, does not further rotate during chronic implantation. Moreover, the configuration and attachment methods should be such as to provide highly reproducible rotational torques so as to maximize productivity in manufacture and minimize scrap and rework. Configurations and methods of attaching suturing rings to annular valve bodies to satisfy these requirements are disclosed in the prior art, e.g., those described in the above-referenced '240 patent and in U.S. Pat. Nos. 5,071,431, 5,397,346, 5,876,436, 6,113,632 for example. However, none of the current available tissue valves allows a surgeon to rotate the stent within the suturing ring because the suturing ring is an integral part of the stent.

Most suturing rings are formed of a radiopaque stiffening ring or band formed of stainless steel or titanium having an inner annular wall and an outer wall extending between axial ends of the band. The fabric is affixed either to the outer wall of the stiffening band as disclosed, for example, in the above-referenced '632 patent or surrounds the stiffening band as disclosed, for example, in the above-referenced '240 patent. The stiffening band of the '240 is a split band formed with split ends that are drawn against one another during assembly of the suturing ring about the valve stent or body to reduce the inner diameter of the split band in order to overcome difficulties encountered in fabrication employing a continuous ring or band that are described in detail in the '240 patent. The split ends are held together by a cord or heat shrink band or shape memory alloy band that is encased within the fabric when the fabric is sutured together. The interior space within the fabric can be filled with an elastomeric compound.

Separation of the finished suturing ring from the valve body or valve stent to replace the mechanical or tissue valve is not suggested in the '240 patent. Any attempt to do so by cutting the suturing ring assembly apart where the split ends abut one another would effectively destroy the suturing ring. Moreover, it would not be possible to locate the split ends beneath the fabric without disassembling the fabric as well as the cord or band.

Despite improvements in longevity, adverse reactions and complications with implanted mechanical heart valves and tissue valves of the types described above requiring surgical replacement can occur from time-to-time during the lifetime of a patient. It has long been recognized that it is desirable to avoid removing and replacing the suturing ring if it is intact and is not implicated in the adverse reaction or complication. Removal of the existing sutures to remove the suturing ring and restitching of a new suture ring in place can compromise the integrity of the valvar rim and lead to further recovery complications, morbidity and mortality. Therefore, attachment and detachment structures and methods have been proposed to enable the removal of the defective mechanical or tissue valve from the suturing ring and insertion of a replacement mechanical or tissue valve into the annulus of the suturing ring sutured to the valvar rim.

In one approach disclosed in the above-referenced '128 patent, the valve stent is sutured to the suturing ring upon initial implantation. Replacement of the tissue valve involves severing the sutures by a scalpel worked between the suturing ring annulus, withdrawing the released tissue valve, inserting a new tissue valve into the ring annulus and suturing it in place. This approach requires a valve design that can be stitched in place in the suturing ring annulus, does not allow the tissue valve to be easily rotated in the suturing ring in the manner described above, and requires considerable care and time to execute. Pannus overgrowth and calcification of the surfaces at the junction between the valve stent and the suturing ring occur over time that must be cut away or through without damaging the suturing ring. Consequently, other approaches have been devised allowing rotation of the replacement tissue or mechanical valve within the suturing ring annulus.

A detachable suturing ring having a shape-memory member that expands in diameter when cooled below blood temperature to allow release and replacement of a valve body or stent is disclosed by J. Jansen et al. in "Detachable Shape-Memory Sewing Ring for Heart Valves", (*Artificial Organs*, vol. 16, No. 3, pp. 294-7, 1992). While this approach would appear to be very beneficial, it has not been established that the temperature induced shape changes are robust enough to assure retention of the tissue or mechanical valve or large enough when cooled by cooling fluid to expand a chronically implanted suturing ring to allow removal of a valve body or stent. Pannus overgrowth and calcification about the suturing ring would likely reduce the amount of expansion or prevent any appreciable expansion of the ring when it is cooled in the attempt to expand it. Moreover, this concept is impractical because of high cost and difficulty in fabrication.

More typically, it has been proposed to use an interlocking mechanism of the suturing ring and the valve body or stent that can be operated by the surgeon to detach or attach valve body or stent from or to the suturing ring. Mating male and female screw threads, snaps, fabric hooks, screws, or other interlocking mechanisms are disclosed in the above-referenced '031 patent, '923 patent, '541 patent, and in U.S. Pat. Nos. 3,997,923, 4,078,268, 4,506,394, 4,705,516, 4,790,843, 6,217,611 and Re.31,040, for example.

These interlocking mechanisms necessarily must be robust enough to ensure that they do not fail during chronic implantation thereby loosening or releasing the tissue or mechanical valve and endangering the life of the patient. The interlocking mechanisms must be large enough to be readily manipulated and to not become frozen due to coagulation or exposure to blood and fluids. On the other hand, the interlocking mechanism must be minute in size in order to avoid taking up space that would reduce the size of the valve annulus or interfere with leaflet function. Consequently, none of these proposed interlocking mechanisms have been adopted.

In the following description and claims, the term "heart valve mechanism" embraces a tissue valve mechanism comprising a stent supporting tissue leaflet(s) and a mechanical heart valve mechanism comprising a heart valve body supporting a pivotal disk or leaflet(s). For convenience, the term "valve frame" means a stent of a tissue valve or a valve body of a mechanical heart valve or equivalents thereof, and the term "occlude" means tissue leaflets of a tissue valve or pivotal disk or leaflets of a mechanical heart valve or equivalents thereof. The assembly of a tissue or a mechanical heart valve mechanism with a suturing ring can be characterized as a heart valve prosthesis.

Thus, there remains a need for improvements in suturing rings that facilitate the initial implantation and replacement of chronically implanted heart valve mechanisms supported by the suturing rings. Among other things, there remains a need for suturing rings that are separable from the heart valve mechanisms that can accommodate a variety of heart valve mechanisms including either tissue valves or mechanical heart valves of differing designs and that are highly versatile in use including potential use in minimal invasive surgery techniques. There remains a need for such suturing rings that have a locking mechanism that does not add bulk to the suturing ring or diminish the suturing ring and valve annulus, that are simple to manufacture and use, and that are robust, durable and reliable. There remains a need for a separate suturing ring that facilitate surface modification of the suturing ring fabric without affecting tissue valve leaflets and that is free of glutaraldehyde employed to preserve the tissue leaflets prior to implantation.

SUMMARY OF THE INVENTION

The present invention is directed toward providing an improved interlocking mechanism and methods of interlocking a suturing ring with a valve frame of a valve mechanism that facilitates the initial implantation and replacement of a chronically implanted heart valve mechanism supported by the suturing ring, that is robust, that does not diminish the valve annulus, and that provides enhanced durability, reliability, ease of use during initial implantation and during replacement surgery, and simplified manufacture. Other advantages of the present invention will be made apparent in the following.

In accordance with a first aspect of the invention, the suturing ring annulus is adjustable to receive and engage the valve frame of the heart valve mechanism within the annulus. An interlocking mechanism applies restraint to fix the adjusted suturing ring annulus engaged against the valve frame to support the heart valve mechanism during chronic implantation.

The surgical steps of initially implanting a tissue valve or mechanical valve of the present invention are greatly simplified by the present invention. Moreover, the surgeon can employ the optimal one of several alternative ways of initially implanting the suturing ring to a valvar rim. The valve frame is inserted into the suturing ring annulus while adjusting the suturing ring annulus to seat the valve frame within the suturing ring annulus and operating the interlocking mechanism to apply restraint to the adjusted suturing ring annulus in seated engagement against the valve frame to retain the valve frame in the suturing ring annulus during chronic implantation of the heart valve prosthesis. The suturing ring can be sutured to the valvar rim either before or after inserting the valve frame in the suturing ring annulus or operating the interlocking mechanism.

The surgical steps of replacing a tissue valve or mechanical valve at a later time are also greatly simplified by the present invention. A dysfunctional valve mechanism is removed from the suturing ring annulus by operating the interlocking mechanism to release the applied restraint, unseating the heart valve frame from the suturing ring annulus, and removing the dysfunctional heart valve prosthesis from the suturing ring annulus. The valve frame or integral suturing ring of a replacement new heart valve mechanism is inserted into the suturing ring annulus while adjusting the suturing ring annulus to seat the valve frame within the suturing ring annulus. The interlocking mechanism is then operated to apply restraint to the adjusted suturing ring annulus in seated engagement against the valve frame to retain the valve frame in the suturing ring annulus during chronic implantation of the replacement heart valve prosthesis. Advantageously, this process allows the dysfunctional valve mechanism to be replaced by the same or a different type of heart valve mechanism.

In another approach, the chronically sewn-in suturing ring can also be used as a "docking station" for an incompatibly dimensioned heart valve prosthesis that comprises a valve mechanism supplied with an integral suturing ring about the valve frame. In this case, the integral suturing ring of the new valve prosthesis can be placed within or over the annulus of the chronically sewn-in suturing ring and sutures can be sewn through them to join them together.

In a preferred embodiment, a suturing ring is formed of a generally annular, split stiffening band extending between opposed band split ends to which a suturing ring fabric is attached. The band split ends are separated apart by a gap such that a first annulus diameter of the annulus of the suturing ring is defined when the suturing ring is unrestrained. The suturing ring is adapted to be surgically attached, as by suturing, to a prepared valvar rim of a patient's heart with the suturing ring unrestrained. The suturing ring first annulus diameter is sized to enable a valve body of a mechanical heart valve or a stent of a tissue valve or other valve frame to be inserted into the suturing ring annulus and rotated therein to a desired orientation. The suturing ring annulus diameter can be increased manually or by an instrument to receive the valve frame.

The band split ends can then be restrained such that a second interior diameter of the suturing ring is defined when the suturing ring is restrained that interference fits with and engages the valve frame exterior surface. An interlocking restraint is preferably accomplished by one or more of sutures, clamps, hooks, teeth, buttons, or other locking mechanisms that can be released even after chronic implantation so that the heart valve mechanism can be replaced.

A preferred restraint comprises the use of one or more suture attached to suture retention mechanisms at the first and second band split ends. The suture can be sewn through a suture hole extending through each one of the opposed band split ends and the suture ring fabric overlying the suture holes. The suture ends are drawn tight to draw the band split ends toward one another, and the suture ends are either tied off or thermally welded together. Preferably, the fabric is marked or colored to indicate where the suture is located.

Preferably, the interior surface of the split stiffening band is shaped in a complimentary mating fashion to the exterior surface of the valve frame to entrap or lock the surfaces together when the band split ends are drawn together and restrained.

Moreover, the valve replacement process of the present invention advantageously preserves the healed annulus and the healed suturing ring, is faster and relatively easier than surgically cutting away the suturing ring and replacing it, and should reduce morbidity and mortality associated with current replacement procedures In a further aspect of the invention, the sewing of the suturing ring to the valvar rim in the initial implantation is simplified, and suture knots about the suturing ring surface can be eliminated or minimized in size and number. In this aspect, the plurality of sutures that are sewn through the valvar rim around its circumference are extended through the suturing ring annulus and suture segments are entrapped within the space between the suturing ring annulus and the outer wall of the valve frame. Then, the free ends of the sutures are trimmed. The relatively bulky knots that can be foci of coagulation or thrombus formation, can abrade tissue valve leaflets, and can interfere with blood flow or valve operation, are eliminated.

In one simple implementation of this further aspect, the sutures are sewn through suture routing guides for routing a plurality of sutures generally equally spaced apart through the suturing ring annulus. The suture guides can comprise an axial end band or both axial end bands of the suturing ring fabric sewn to the suturing ring that the sutures are sewn through at spaced apart locations around the circumference of the suturing ring so as to support the suturing ring and to maintain the sutures generally evenly spaced apart alongside the stiffening band interior side wall.

In a further implementation of this second aspect, a plurality of spaced apart suture guides are preferably formed in the stiffening band to dispose a plurality of sutures spaced apart from one another and extending within the suturing ring annulus alongside the interior band sidewall. The suture guides can be a plurality of suture holes arrayed around the circumference of the generally annular split stiffening band that facilitate suturing of the suturing ring to the prepared valvar rim. The suture holes preferably extend through at least a portion or portions of the split stiffening band that is or are shaped in a complimentary mating manner to the exterior surface of the valve frame whereby at least a portion of each suture is entrapped therebetween when the band split ends are drawn together and restrained. Alternatively, the sutures can be extended through an array of preformed holes or slots through the split stiffening band that are also used in stitching the suturing ring fabric to the split stiffening band.

The sutures can be routed through the suture guides and a portion of the suturing ring, and the suture ends can be tied by simple single or double hitches that are smaller and easier to tie than square knots tying two suture ends together.

In a preferred embodiment of the further aspect, the interior surface of the split stiffening band is formed with a pair of band flanges extending outwardly from the stiffening band inner surface and spaced apart to define a groove therebetween that is dimensioned to receive an outwardly extending stent flange of the valve frame when the band split ends are drawn together and restrained. A plurality of axially aligned pairs of suture holes are formed through the band flanges arrayed about the circumference of the split stiffening band, whereby one or more suture can be extended through each axially aligned pair of suture holes and across the intervening groove. The sutures can be employed to suture the suturing ring to the valvar rim, and are then entrapped within the groove by the stent flange when the band split ends are drawn together and restrained.

Furthermore, the band flanges are preferably notched to the flange edges at the suture holes to enable the one or more suture to be laterally, rather than axially, inserted into the axially aligned suture holes.

Tissue ingrowth into the interstices of the suturing ring fabric occurs in time, and the sutures may become unnecessary to retain the suturing ring in place. However, it is preferable to create a single hitch or double hitches of the suture ends to the suturing ring fabric. It is therefore possible to employ the chronically implanted suturing ring in the replacement procedures described above.

Alternatively, a single running suture or sets of sutures can be sewn through the suturing ring annulus and adjoining valve rim tissue at multiple points around the circumference of the suturing ring. In this way, multiple segments of the single suture are entrapped between the suturing ring annulus and the valve frame and the number and size of suture hitches are minimized.

A number of advantages can be realized from the above-described first and second aspects of the invention practiced collectively or separately in either or both of an initial implantation of the separate suturing ring and heart valve mechanism or a replacement of a dysfunctional heart valve mechanism in a chronically implanted suturing ring of the present invention.

The above-described procedures for implanting the suturing ring advantageously allows the physician to view the placement of sutures through the open suturing ring annulus rather than having that view blocked by the heart valve mechanism. The suturing of the suturing ring to the valvar rim is greatly simplified, and errors are reduced. Moreover, the procedure may lend itself to minimum invasive surgery techniques.

In addition, the suturing ring collar that sutures are normally sutured through can be eliminated (or minimized to the extent needed to effect proper sealing against the valvar rim). Therefore, the suturing ring can have any shape. Since suturing is through the suturing ring annulus, the surgeon can select a larger diameter suturing ring capable of supporting a larger heart valve mechanism in the suturing ring annulus to optimize valve function.

In yet another aspect of the invention, a heart valve prosthesis has a frame that includes at least one outwardly extending annular flange adjacent to a suturing ring and a band comprising an inwardly extending annular flange that is capable of engagement with the annular flange of the frame. A tortuous path is formed between the annular flange of the frame and the annular flange of the band that can engage and restrain a suture placed between them. One or more split portions or tab portions on the band are adapted to lock the band in engagement with the flange of the frame. Such a device can be used to more easily replace a heart valve by advancing a sutures through a suturing ring on the valve and the valvular rim such that they are brought outward of the flange extending from the frame and advancing the band over the valve and over the sutures at a proximal, outflow end of the valve until the band engages the flange and captures the sutures between the band and the flange. The split portions or tab portions in the band can be used to lock the band to the flange.

Finally, a surgeon can attach the suturing ring to the valve frame and then implant the heart valve prosthesis in the conventional manner. Thus, the suturing ring can be used in a variety of ways meeting the preferences of the surgeon in any particular case.

Tissue valves are supplied immersed in toxic glutaraldehyde in sterile containers until they are used. The suturing ring fabric and any elastomeric filler of such conventional tissue valves are also immersed in the glutaraldehyde. During implantation of such tissue valves, it is necessary to rinse the tissue valves for some time to reduce the residual glutaraldehyde. Usually, the valvar rim site is prepared and sized before an appropriately sized tissue valve is selected. Then, the rinsing must take place. The present invention offers the further advantages of supplying the suturing ring in a sterile container devoid of glutaraldehyde, so that it does not require rinsing, and direct contact of residual glutaraldehyde with the valvar rim tissue is eliminated. Overall procedure time can be saved in the procedure by attaching the suturing ring to the valvar rim while the tissue valve mechanism is being rinsed.

The fabric covering of suturing rings can also be surface treated during manufacture to reduce calcification or thrombus formation without affecting the heart valve body and occluder(s) or stent and tissue leaflets since they are manufactured separately.

This summary of the invention and the advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other features and advantages of the invention will become apparent to those skilled in the art from the following detailed description of a preferred embodiment, especially when considered in conjunction with the accompanying drawings in which:

FIG. 10 is an illustration of one method of securing the suturing ring to the valvar rim employing sutures through the suturing ring fabric;

FIG. 11 is an illustration of a further method of securing the suturing ring to the valvar rim employing sutures extending inside the suturing ring annulus in accordance with the second aspect of the invention;

FIG. 26a is a perspective view of the band shown in FIG. 25a.

FIG. 26d is a partial perspective view of yet another embodiment of a band similar to that shown in FIG. 26a.

FIG. 28a is a cross sectional view of the engaged band taken at the cross section of FIG. 26b with the frame portion of FIG. 25a.

FIG. 28b is a cross sectional view of the engaged band taken at the cross section of FIG. 26c with the frame portion of FIG. 25a.

FIG. 29a is a perspective view of the band of FIG. 25a engaged with a band applicator tool for applying it to a frame portion as in FIGS. 25a-b.

FIG. 29b is a cross sectional view of the band applicator tool and band of FIG. 29a.

FIG. 30b is a perspective view of the suture tensioning tool of FIG. 30a.

FIG. 31 is a perspective view of the valve and valve holder tool of FIG. 30a with the band and band applicator tool of FIG. 29a.

DETAILED DESCRIPTION OF THE PREFERRED EMBODIMENTS OF THE INVENTION

The present invention can be implemented to improve implantation procedures and performance of a wide variety of heart valve prostheses of the various types currently existing or that may come into existence that are surgically attached to a prepared valvar rim. As noted above, the present invention involves improved suturing rings that support removable heart valve mechanisms, e.g., tissue valves and mechanical heart valves comprising a heart valve frame and occluder. The valve frames described in the exemplary embodiments are a tissue valve stent or a mechanical valve body, and the occluders include tissue leaflets of a tissue valve or pivotal disk or leaflets of a mechanical heart valve. The various aspects of the present invention may be utilized in attaching any such valve frame or any other valve frames that are devised in the future to a suturing ring.

Figure 1:
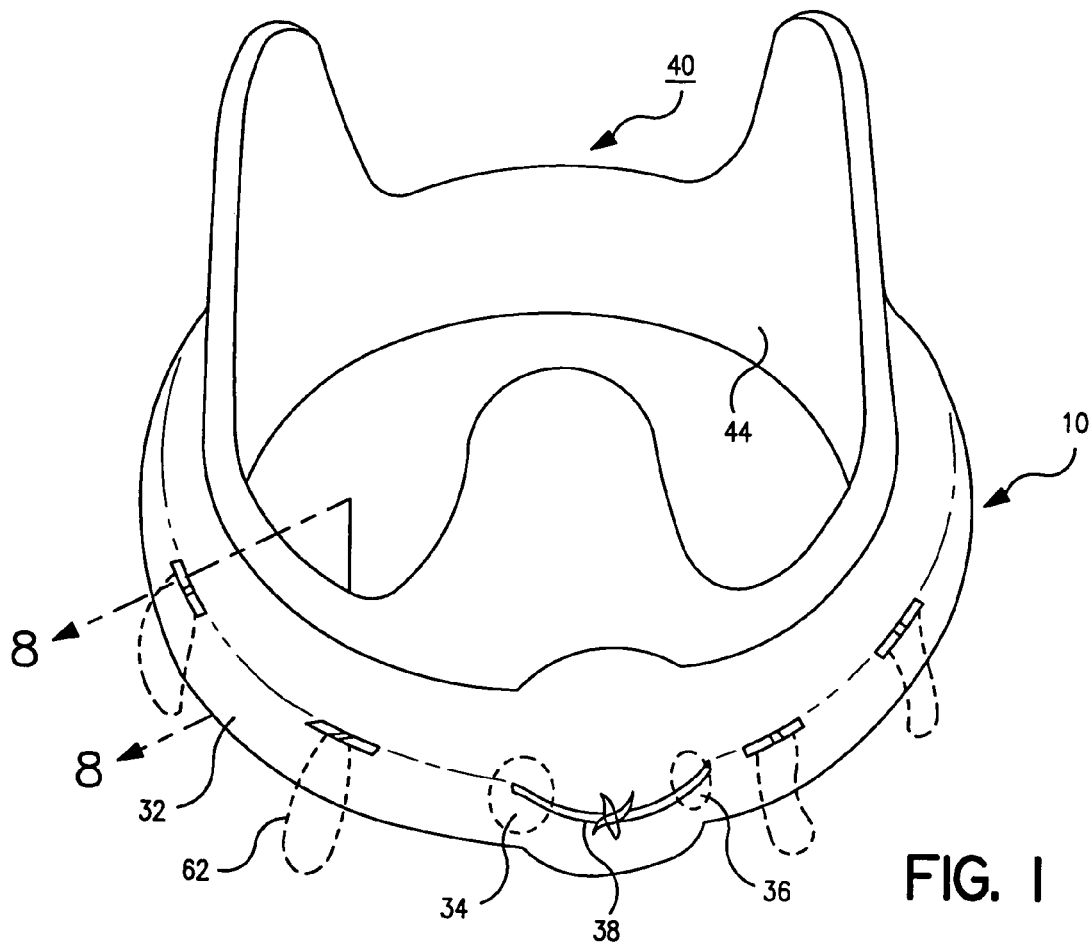
FIG. 1 is a perspective view of the assembly of a suturing ring and stent of a tissue valve formed in accordance with the present invention.
Figure 2:
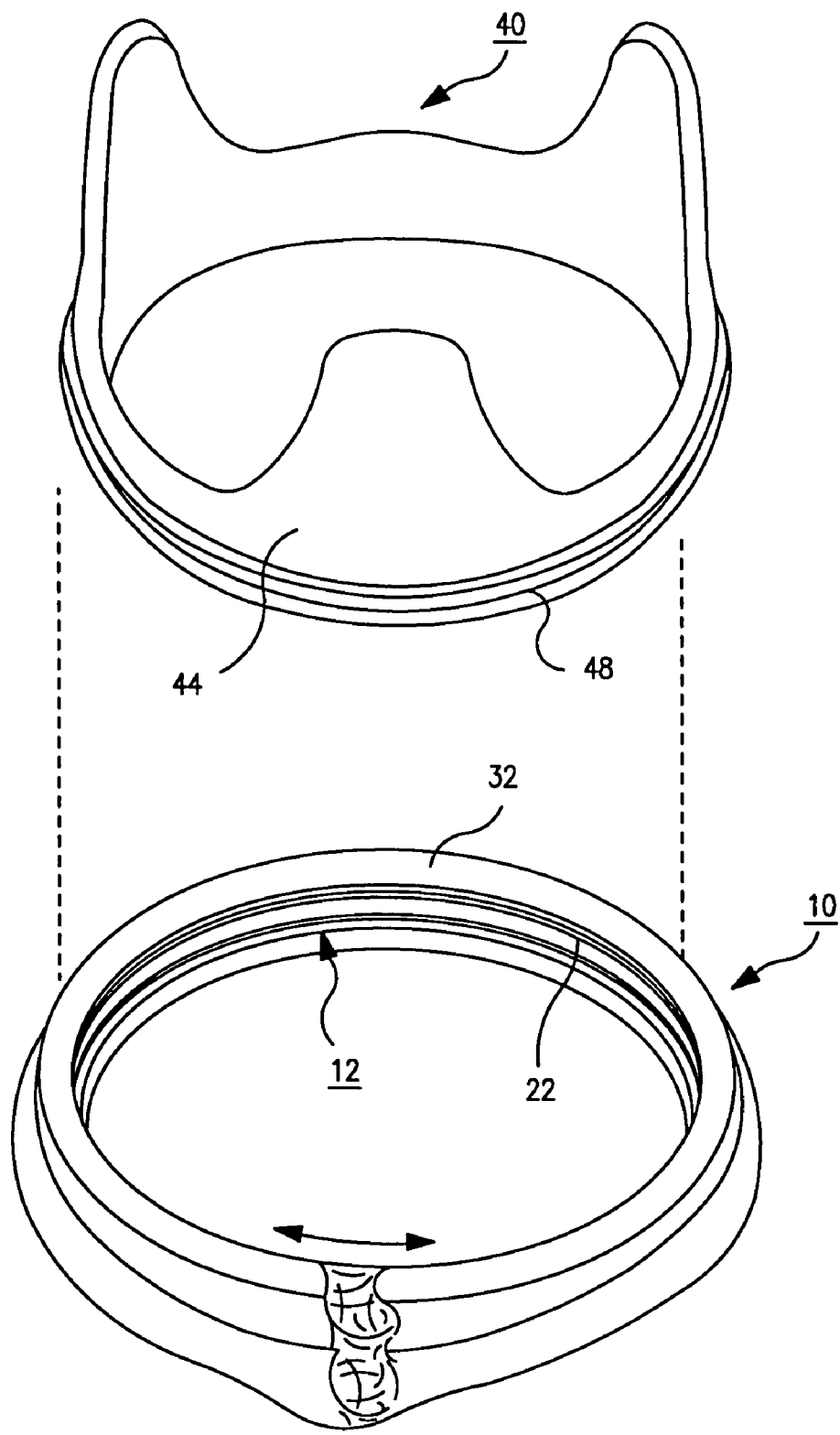
FIG. 2 is a perspective view of the stent of FIG. 1 arranged to be inserted into the annulus of the suturing ring of FIG. 1.
Figure 3:
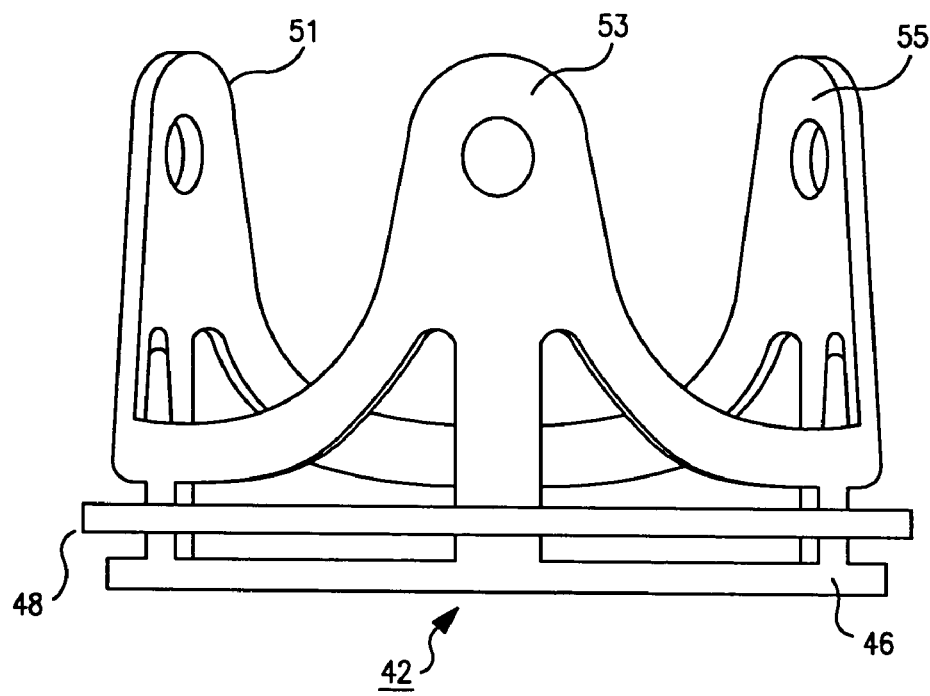
FIG. 3 is a side elevation view of the stent frame of the stent of FIG. 2.
Figure 6:
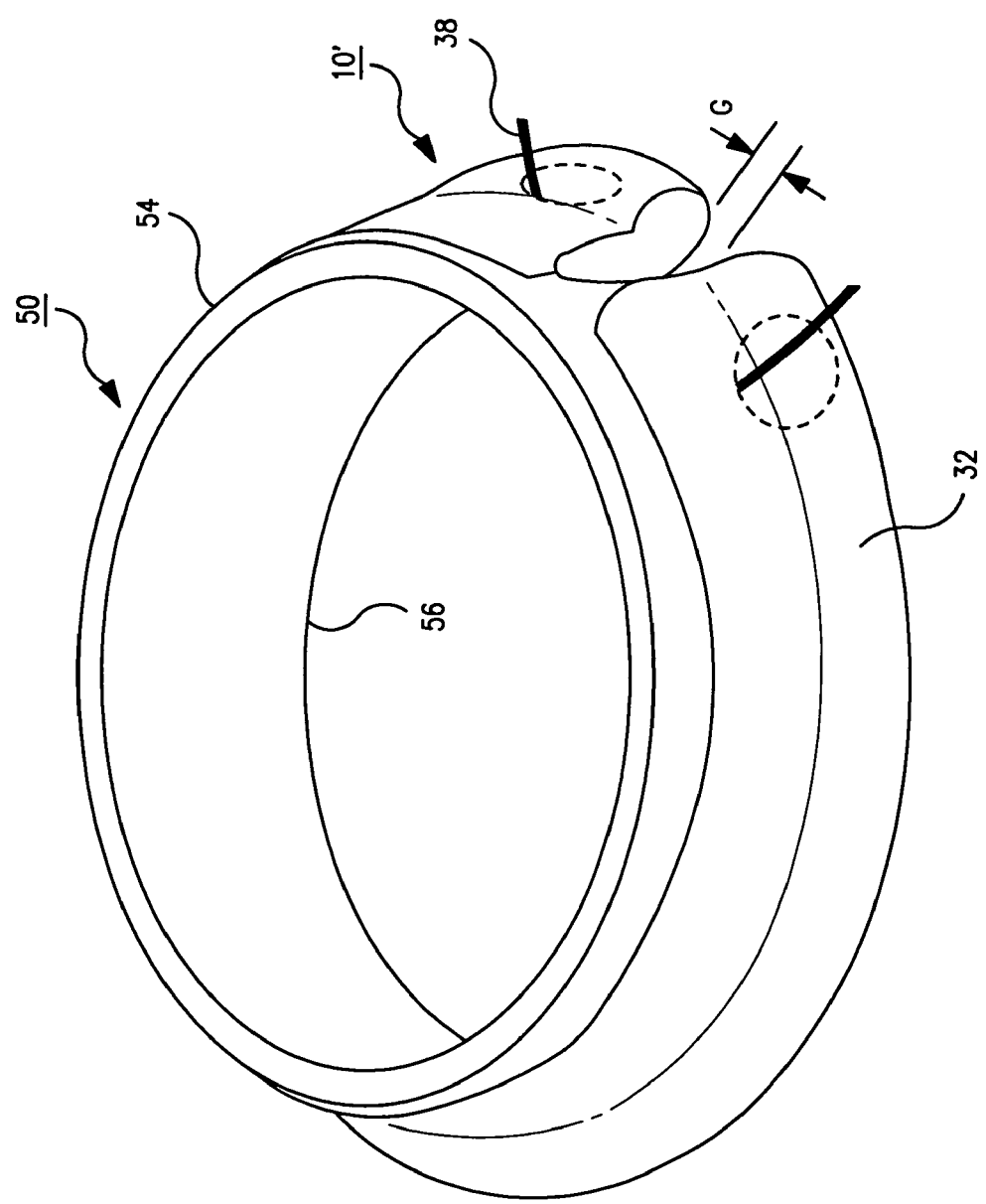
FIG. 6 is a perspective view of the released assembly of a further embodiment of the suturing ring of FIGS. 1 and 2 and a valve body of a mechanical valve formed in accordance with the present invention.
Figure 7:
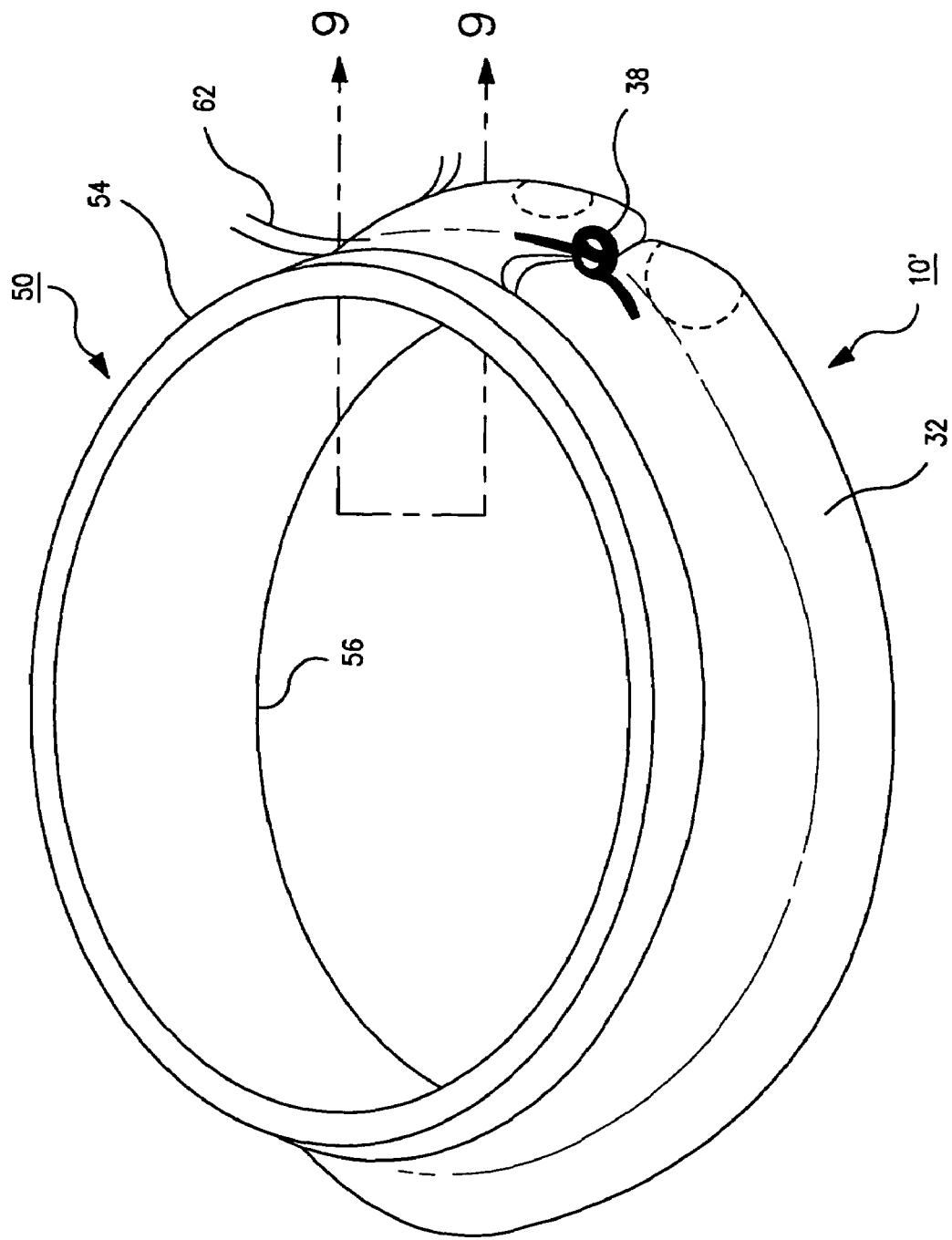
FIG. 7 is a perspective view of the tightened assembly of the suturing ring of FIG. 6 about the outer wall of the valve body of the mechanical valve of FIG. 6.

Thus, for example, FIGS. 1-3 depict a suturing ring 10 that is employed to support a fabric covered stent 40 of a tissue valve mechanism, and FIGS. 6 and 7 depict a suturing ring 10' that is employed to support a valve body 50 of a mechanical heart valve mechanism. The tissue leaflets supported by stent 40 are not show in the figures for convenience of illustrating the aspects and embodiments of the present invention. The stent 40 and tissue leaflets can take any of the forms known in the art such as those described in the background of the invention. Similarly, the pivotal disk or leaflet(s) and the valve seat and the hinging mechanisms of the valve body 50 enabling and controlling movement of the pivotal disk or leaflets may take any of the forms known in the art and are not shown in any of the figures for convenience of illustrating the aspects and embodiments of the invention.

Figure 5:
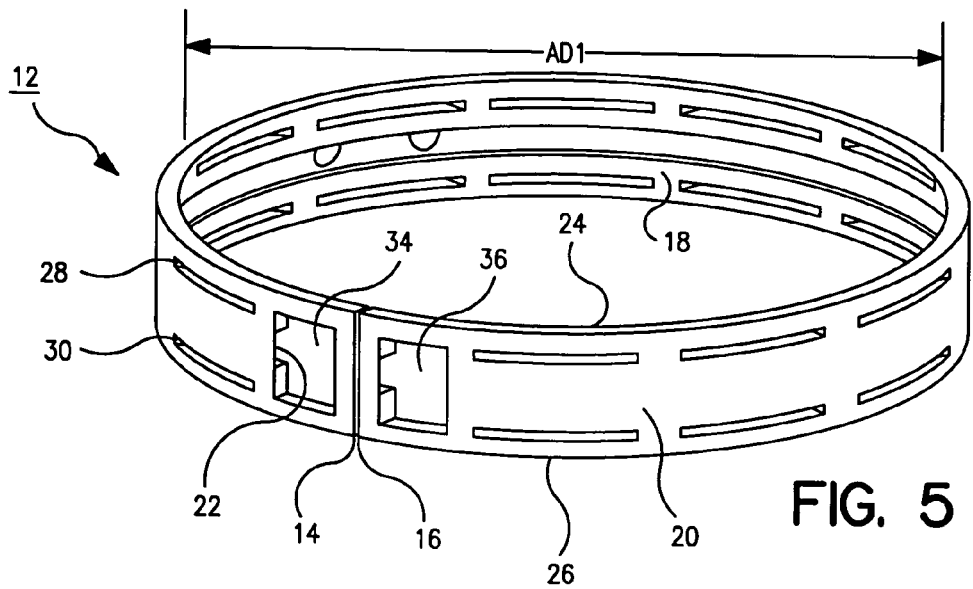
FIG. 5 is a perspective view of the split stiffening band enclosed within the suturing ring of FIGS. 1 and 2.
Figure 4:
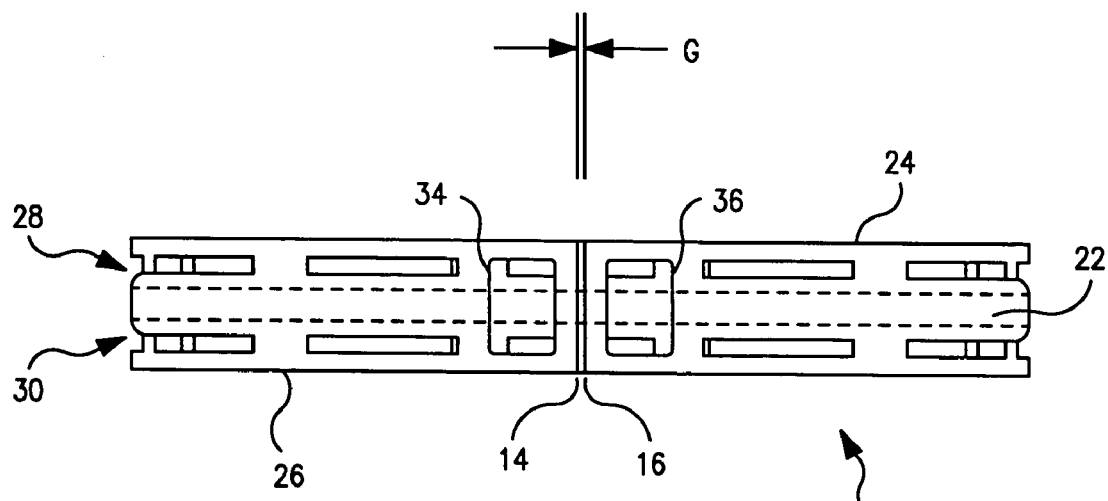
FIG. 4 is a side elevation view of the split stiffening band enclosed within the suturing ring of FIGS. 1 and 2.

In the first aspect of the present invention, the suturing rings 10 and 10' are formed of a generally annular, split stiffening band 12 depicted in FIGS. 2, 4 and 5 extending longitudinally between opposed band split ends 14 and 16 and that supports a stent fabric 32. The split stiffening band 12 can be formed of a biocompatible metal, e.g., titanium or tantalum, a plastic material, e.g., Delrin® plastic, reinforced pyrolytic carbon or of other material. The split stiffening band 12 has an interior band sidewall 18 formed with an outwardly extending annular groove 22 that engages the stent 40 as described further below and an exterior band sidewall 20 that is generally flat but may have any shape. The inner and exterior band sidewalls 18 and 20 are joined at the opposed band split ends 14 and 16 and at the upper and lower axial ends 24 and 26. A plurality of upper and lower suture receiving slots 28 and 30 extend through the inner and exterior band sidewalls 18 and 20 so that the suturing ring fabric 32 can be sutured to the split stiffening band 12.

The suturing ring fabric 32 comprises a fabric strip made of synthetic fiber, such as polytetrafluoroethylene (e.g., "Teflon TFE") or polyester (e.g., "Dacron"), of a mesh weave having interstices permeable to tissue ingrowth. The longitudinal edges of the fabric strip are sewn together to form longitudinal seams. One longitudinal seam is wrapped over the upper axial end 24, fitted against the interior band sidewall 18 over the set of upper slots 28, and the fabric strip is sewn together through the set of upper slots 28. The other longitudinal seam is wrapped over the lower axial end 26, fitted against the interior band sidewall 18 over the set of lower slots 30, and the fabric strip is sewn together through the set of lower slots 30. The ends of the fabric strip are sewn together over the gap G (FIG. 4) separating the opposed band split ends 14 and 16 in the suturing ring 10 or left separated at the opposed band split ends 14 and 16 in the suturing ring 10'. In this way, groove 22 remains exposed, and the fabric strip is thereby formed into a torus shaped or annular shaped suturing ring fabric 32. The shape of the suturing ring fabric 32 may be relatively flat if the suturing ring is intended to be used in aortic valve replacement as shown in the above-referenced '575 patent. Suturing rings for heart valves intended for mitral valve replacement have pronounced radially extending flanges or skirts or collars formed of a wider fabric strip that is sewn or filled as shown, for example, in the above-referenced '030 and '346 patents, respectively. The suturing ring fabric 32 may also be filled with a biologically acceptable, spongy material, such as silicone rubber or polyurethane or hydrogel, and the filled suturing ring fabric 32 may be formed and shaped as desired. However, the resulting suturing ring fabric 32 may have any desired cross-section profile.

As shown in FIG. 4, the band split ends 14 and 16 are separated apart by a gap G such that a first annulus diameter AD1 of the annulus of the suturing ring 10 is defined when the suturing ring 10 is unrestrained. The split stiffening band 12 is resilient, and the split stiffening ends 14 and 16 can be separated apart to widen gap G and increase the first annulus diameter AD1 to a second annulus diameter AD2 that accommodates a somewhat larger diameter valve frame or brought together to decrease gap G and the first annulus diameter AD1 to the second annulus diameter AD2 to accommodate a somewhat smaller diameter valve frame.

The suturing ring 10 is adapted to be surgically attached, as by suturing, to a prepared aortic or mitral valvar rim of a patient's heart with the suturing ring 10 unrestrained as described further below. The suturing ring first annulus diameter AD1 is sized with respect to the selected heart valve frame diameter to enable a valve body 50 of a mechanical heart valve or a stent 40 of a tissue valve to be inserted into the suturing ring annulus and rotated therein to a desired orientation. Then, the suturing ring split ends 14 and 16 are secured or restrained by an interlocking or restraining mechanism of one of the types described herein and equivalents thereto. The restraint is preferably accomplished by one or more of sutures, clamps, hooks, teeth, buttons, or other ring locking mechanisms that can released even after chronic implantation so that the heart valve mechanism can be replaced.

A preferred interlocking restraint comprises the use of one or more suture 38 sewn through the fabric 32 overlying and through a suitable suture retainer, e.g., the illustrated suture holes 34 and 36 extending through the stiffening band 12, adjacent the band split ends 14 and 16, respectively. The suture 38 is pulled tight to draw the band split ends 14 and 16 together to the extent permitted by the valve frame, and tied off. Thus, the stiffening band split ends 14 and 16 can be restrained such that the second annular diameter AD2 of the suturing ring 12 is defined, and the suturing ring 12 interference fits with and engages the valve frame exterior surface. In the following examples, it will be assumed that the second annulus diameter AD2 is smaller than the first annulus diameter AD1.

Preferably, the interior surface 18 of the split stiffening band 12 is shaped in a complimentary mating fashion to the exterior surface of the valve frame to entrap or lock the surfaces together when the band split ends 14 and 16 are restrained. For example, it will be assumed that the complimentary mating shapes can comprise one or more spiral or annular groove or array of groove segments or pin holes extending into the outer surface of the valve frame or into the inner surface 18 of the split stiffening band 12 that receives a mating one or more spiral or annular flange or array of flange segments or pins projecting outward from the other of the inner surface 18 of the split stiffening band 12 or the outer surface of the valve frame.

In the depicted tissue valve embodiments, the valve stent 40 comprises a wire or plastic or reinforced pyrolytic carbon stent frame 42 covered with stent fabric 44 of the same materials as the suturing ring fabric 32. The stent frame 42 shown in FIG. 3 can take any of the known configurations having a cylindrical frame base 46 and a plurality of frame posts 51, 53, and 55. An annular flange 48 is formed extending outward of the frame wall around the cylindrical frame base 46 that is dimensioned to be seated and retained in the annular groove 22 of the split stiffening band 12. The stent fabric 44 is sewn together to extend all over the interior surface of the stent frame 42, over the exterior surface of the posts 51, 53, and 55 and sewn together along either side of the stent flange 48, leaving the stent flange 48 exposed.

An alternate suturing ring 10' is depicted in FIGS. 6 and 7 that differs from suturing ring 10 only in that the fabric strip ends of the suturing ring fabric 32 are not sewn together over the band split ends 14 and 16, whereby the suturing ring 10' itself has split ends. Certain of the interlocking mechanisms contemplated by the invention may require direct access to the band split ends 14 and 16 in order open and close the restraints. The suture 38 can be used to interlock and restrain the band split ends 14 and 16 when the suturing ring fabric is sewn together as in suturing ring 10 shown in FIG. 1 or is not sewn together as in alternate suturing ring 10' shown in FIG. 7.

Figure 8:
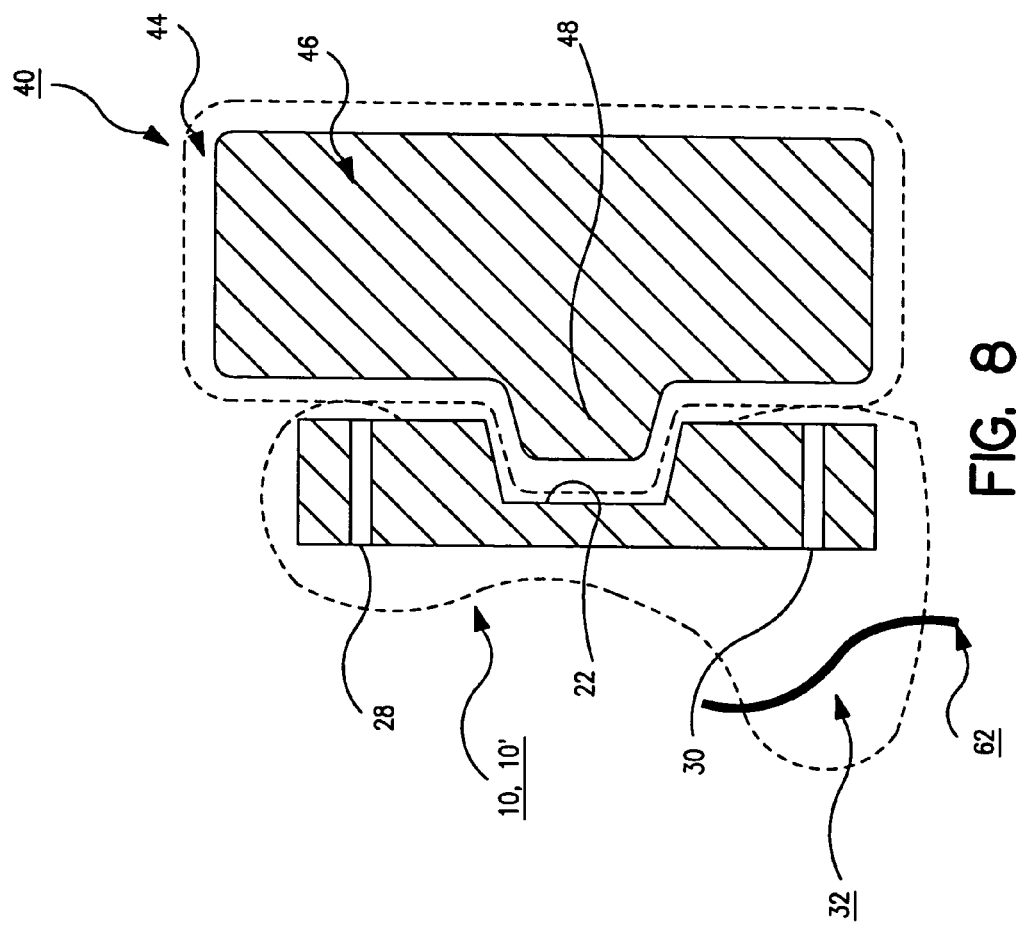
FIG. 8 is a cross-section view taken along lines 8-8 of FIG. 1 illustrating the mating engagement of the fabric covered split stiffening band of the suturing ring against the outer wall of the fabric covered stent.

FIG. 8 is a cross-section view taken along lines 8-8 of FIG. 1 illustrating the mating engagement of the fabric covered split stiffening band 12 of the suturing ring 10 or 10' against the outer wall of the fabric covered valve stent frame 46. In particular, the exposed annular flange 48 fits into the exposed band groove 22 in an interference fit that holds the stent 40 firmly but enables the stent 40 to be rotated when sufficient torque is applied to it during surgery.

Figure 9:
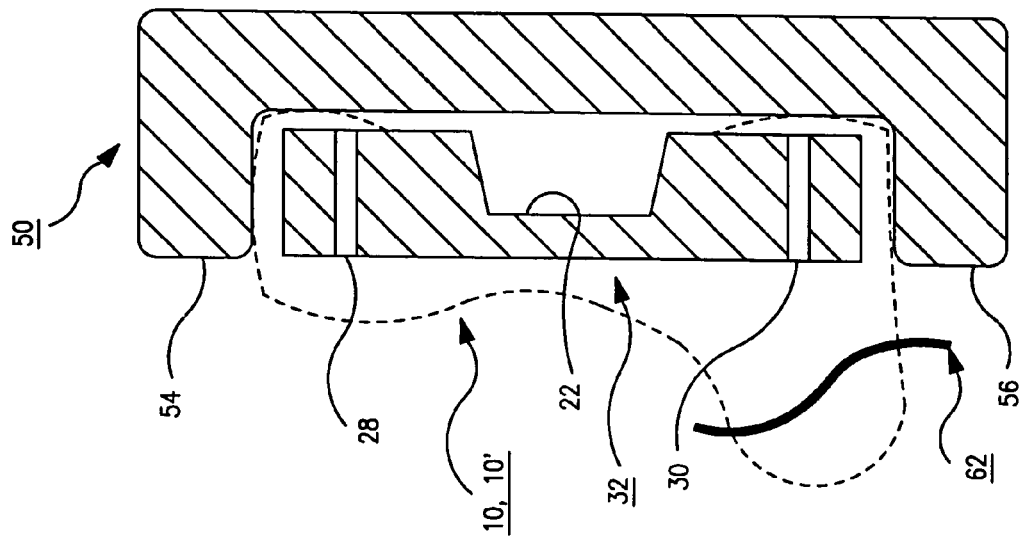
FIG. 9 is a cross-section view taken along lines 9-9 of FIG. 7 illustrating the mating engagement of the fabric covered split stiffening band of the suturing ring against the outer wall of the valve body.

The particular configuration of the suturing ring 10 enables suturing ring 10 or alternate suturing ring 10' to be used to engage and retain a conventional mechanical heart valve body 50 of the type depicted in FIGS. 6 and 7. The simplified depiction of the valve body 50 shows that the valve body outer wall 52 is cylindrical between upper and lower outwardly extending flanges 54 and 56. The annulus diameter AD2 and the width of the suturing ring 10 or 10' between axial ends 24 and 26 are selected so that the interior band sidewall 18 is seated and retained within the U-shaped annular channel formed between the upper and lower flanges 54 and 56. The inwardly extending groove 22 does not play any role in or interfere with retention of the suturing ring 10 or 10' within the U-shaped annular channel formed between the upper and lower flanges 54 and 56 as shown in FIG. 9.

The surgical steps of initially implanting a tissue valve or mechanical valve of the present invention are greatly simplified by the present invention. The surgical method comprises first surgically exposing and excising the dysfunctional native heart valve and preparing the valvar rim 60 shown in FIG. 10 in the conventional manner. An array of sutures 62 is extended through the valvar rim tissue and the suturing ring fabric 32 as shown in FIG. 10. The suturing thread is passed through the valvar rim tissue and then returned through the fabric 32. If desired, pledgets may be used to reduce the possibility of cutting or tearing the tissue when tightening the sutures 62. In this situation, double armed sutures are first passed through the valvar rim tissue and then through the suturing ring fabric 32.

The suturing ring 10 can then be advanced over the sutures 62 and against the valvar rim 60 while holding the sutures 62 taut. The suture ends are then tied together against the suturing ring fabric to fix the suturing ring 10 in place, and the suture ends are then trimmed. The sutures 62 through the suturing ring fabric 32 are also shown in FIGS. 1, 8 and 9. The connection between the suturing ring 10 and the valvar rim tissue is carefully checked in an effort to prevent development of perivalvular leaks or dehiscence after the heart valve mechanism is in place.

The suturing ring diameter AD1 is expanded if necessary so that the valve frame, e.g., the depicted valve stent 40 or the valve body 50, can then be inserted into the annulus of the suturing ring 10 and seated as described above. The unrestrained suturing ring annulus diameter AD1 is either expanded or compressed to the restrained suturing ring annulus diameter AD2 if necessary to seat the suturing ring 10 about the valve frame. The valve frame can then be rotated to the optimal orientation within the suturing ring 10. The restraint, that is the suture 38 or other interlocking mechanism is then affixed to inhibit any spontaneous rotation or detachment of the valve frame from the suturing ring annulus. The valve function is checked to make certain it is oriented optimally. If further rotation is necessary, it may be necessary to release the restraint, rotate the valve frame, and repeat the restraining steps. The conventional surgical closures are then made.

The initial implantation procedure can be further simplified by inserting the valve frame into the stiffening ring annulus while both are supported above and away from the valvar rim 60 by the extended array of sutures 62 held taut during the procedure. Thus, the valve stent 40 can be inserted into the annulus of the suturing ring 10 as shown in FIG. 10, and the assembly can be advanced over the taut array of sutures 62 to seat the suturing ring 10 against the valvar rim 60. The valve stent 40 can still be rotated within the suturing ring annulus to the optimal orientation before or after the suturing ring 10 is sutured against the valvar rim 60 and the restraint is affixed to the band split ends 14 and 16.

Figure 12:
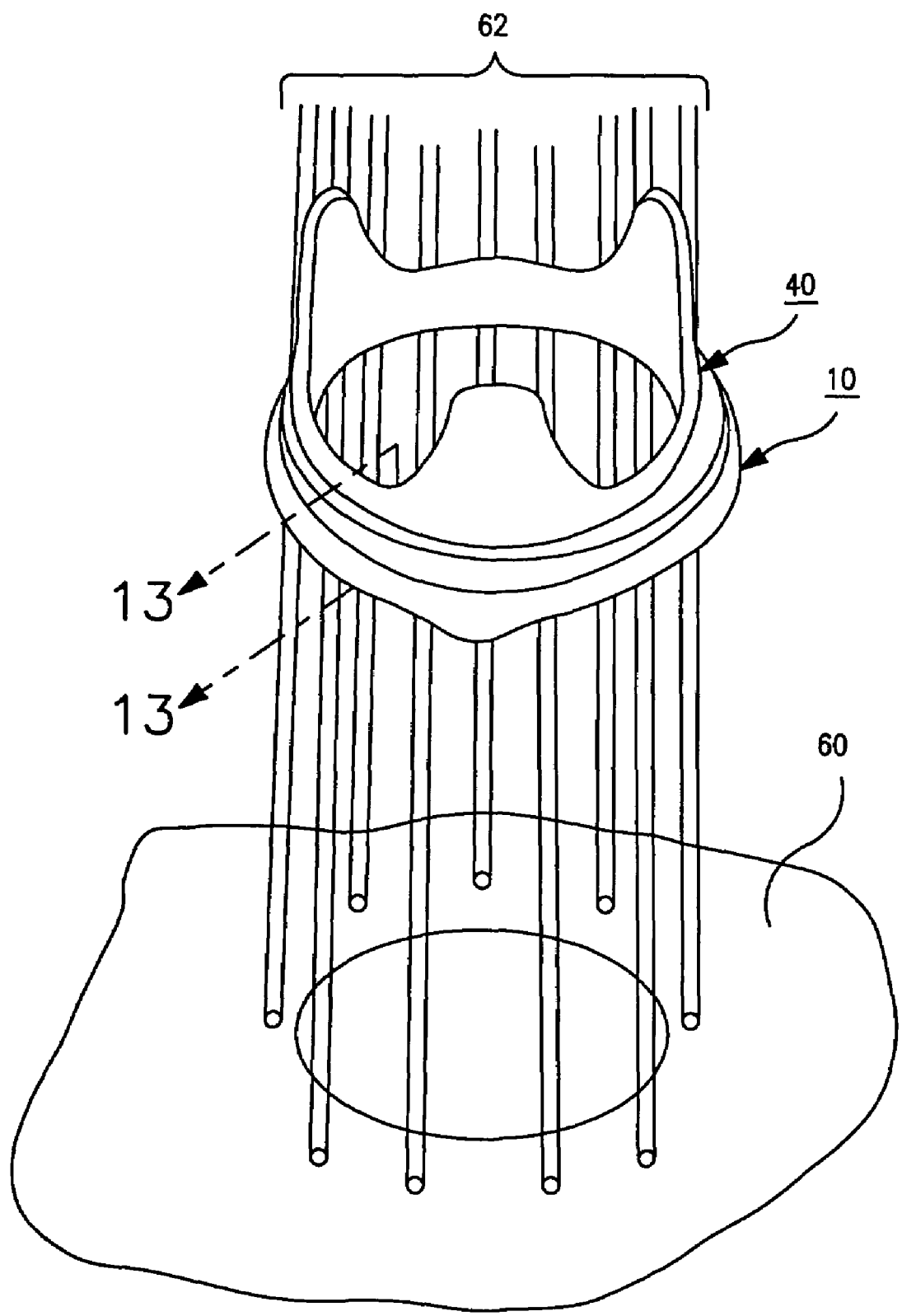
FIG. 12 is an illustration of the valve stent seated into the suturing ring annulus enabling the assembly to be advanced along the taut sutures and seated firmly against the valvar rim when the fabric covered, split stiffening band is restrained and the sutures are entrapped between the suturing ring inner wall and the stent outer wall.

In a further aspect of the invention, the sewing of the suturing ring to the valvar rim in the initial implantation steps is simplified such that suture knots about the suturing ring surface can be eliminated. In this aspect, the plurality of sutures 62 that are sewn through the valvar rim 60 around its circumference are extended through the suturing ring annulus (at least in part) as shown in FIG. 11. The sutures 62 are entrapped between the suturing ring annulus and the outer wall of the valve frame in the subsequent steps, e.g., by the valve stent 40 as shown in FIG. 12. The valve stent 40 can be inserted into the annulus of the suturing ring 10 as shown in FIG. 12, and the assembly can be advanced over the taut array of sutures 62 to seat the suturing ring 10 against the valvar rim 60. The valve stent 40 can still be rotated within the suturing ring annulus to the optimal orientation before or after the suturing ring 10 is sutured against the valvar rim 60 and the restraint is affixed to the band split ends 14 and 16. The free ends of the sutures 62 are then trimmed down to the surface of the suturing ring fabric 32 in the final implantation step prior to closure. The relatively bulky knots that can abrade tissue valve leaflets, be foci of coagulation or thrombus formation, and can interfere with blood flow or valve operation are eliminated.

It will be understood that a mechanical valve mechanism can be substituted for the tissue valve mechanism schematically illustrated in FIGS. 10-12.

In one simple implementation of this further aspect, the sutures 62 are sewn through an axial end band or both axial end bands of the suturing ring fabric 32 at spaced apart locations around the circumference of the suturing ring 10 so as to support the suturing ring 10 and to maintain the sutures generally evenly spaced apart. Then, the exposed ends of the sutures extending out of the suturing fabric 32 can be tied off.

Alternatively, each of the sutures 62 can be extended through the suturing fabric 32 and through an array of suture guides formed in or supported by the split stiffening band 12. For example, the sutures 62 can be sewn through the preformed holes or slots 28 through the split stiffening band 12 that are also used in stitching the suturing ring fabric 32 to the split stiffening band 12. The sutures 62 are brought up from the valvar rim 60 through the suturing ring annulus and then extended outward via an attached suture needle (not shown) through the overlying suturing ring fabric 32 and preformed holes or slots 28, back inward around the suturing ring fabric 32 overlying the band axial end 24, and then back outward through the overlying suturing ring fabric 32 and preformed holes or slots 28. Conversely, the sutures 62 are brought up from the valvar rim 60 through the suturing ring annulus, brought outward around the suturing ring fabric 32 overlying the band axial end 24, then extended via the attached suture needle back inward through the overlying suturing ring fabric 32 and preformed holes or slots 28, and then back outward around the suturing ring fabric 32 overlying the band axial end 24.

Figure 14:
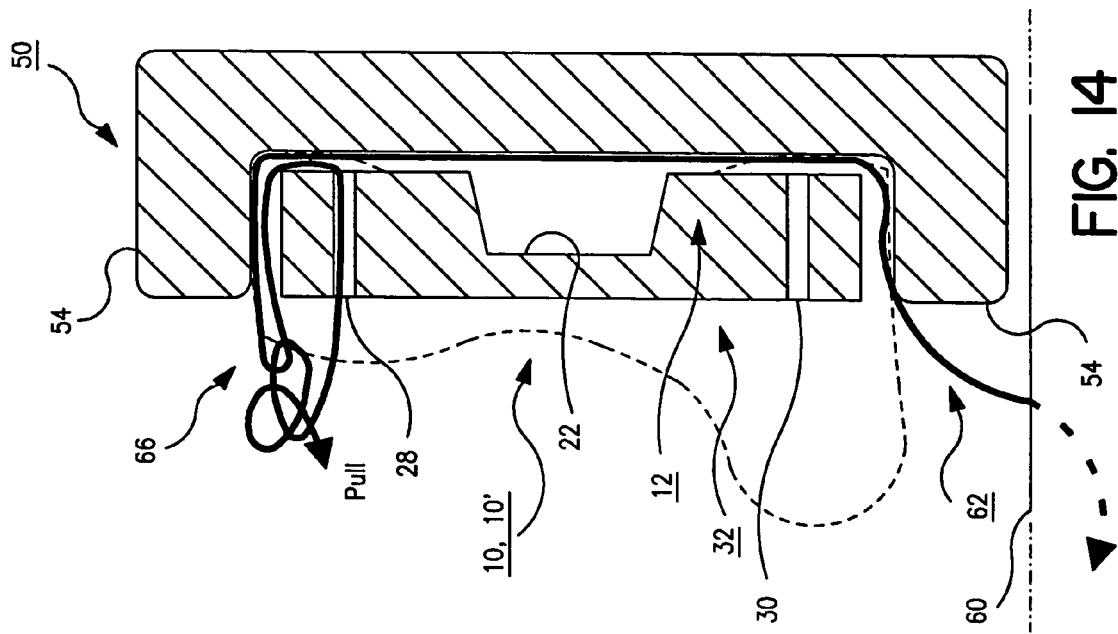
FIG. 14 is a further cross-section view taken along lines 9-9 of FIG. 7 illustrating the entrapment of a suture between the inner wall of the suturing ring and the outer wall of the valve body of a mechanical heart valve.
Figure 13:
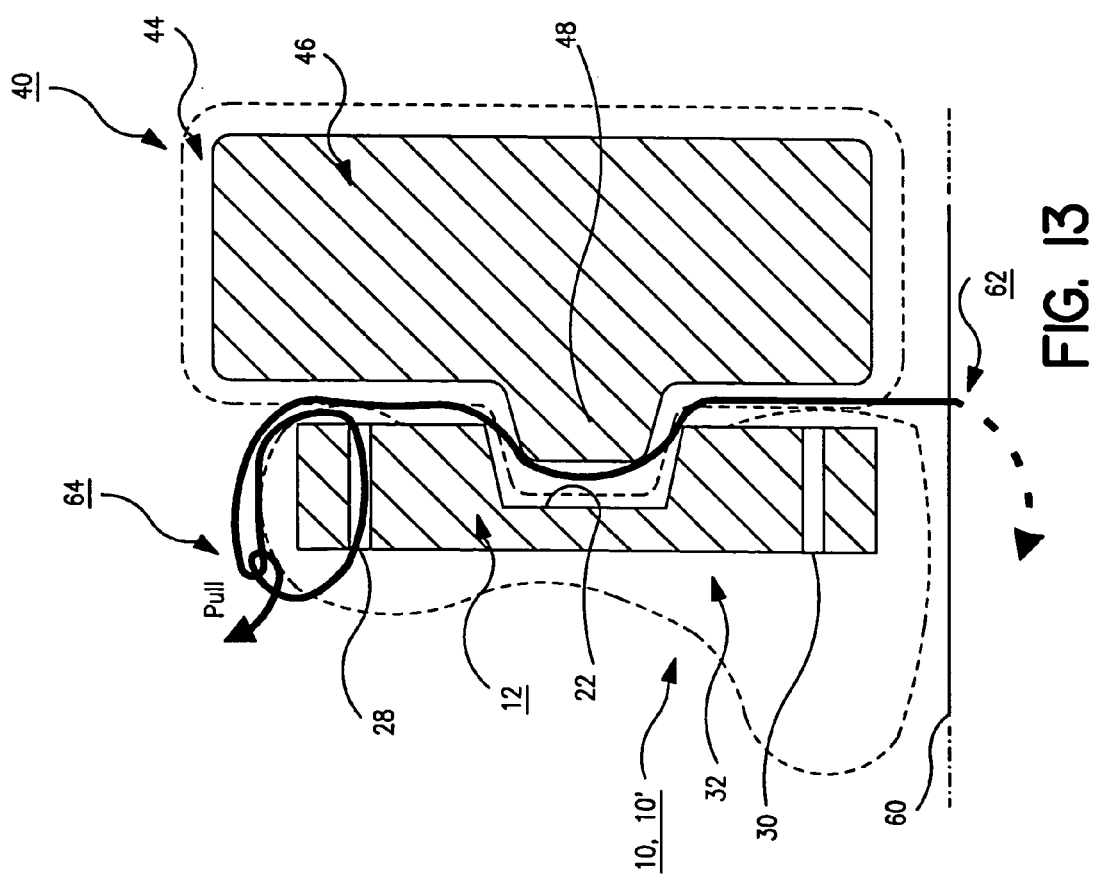
FIG. 13 is a cross-section view taken along lines 13-13 of FIG. 12 illustrating the entrapment of a suture between the inner wall of the suturing ring and the outer wall of the stent.

FIG. 13 illustrates the entrapment of a suture 62 extending from the valvar rim 60 between the inner wall of the suturing ring 10, 10' and the outer wall of the stent 40, particularly illustrating the seated stent flange 48 within the suturing ring groove 22. Advantageously, the free ends of the sutures 62 can routed through the suturing ring fabric 32 and upper suture grooves or holes 28, around the upper band axial end 24 and suturing ring fabric 32, pulled tight to affix the suturing ring 10, 10' snugly against the valvar rim 60, and tied off using a single hitch 64 as shown in FIG. 13. FIG. 14 illustrates the entrapment of a suture 62 extending from the valvar rim 60 between the inner wall of the suturing ring 10, 10' and the outer wall of the mechanical valve body 50, particularly illustrating the suturing ring 10, 10' seated in the U-shaped channel of the valve body 50 as described above. The free ends of the sutures 62 can routed through the suturing ring fabric 32 and upper suture grooves or holes 28, around the upper band axial end 24 and suturing ring fabric 32, pulled tight to affix the suturing ring 10, 10' snugly against the valvar rim 60, and tied off using a double hitch 66 as shown in FIG. 14. The single hitch 64 or double hitch 66 can be efficiently made by the surgeon manipulating the suturing needle to make the hitch loop(s), pulling the sutures 62 tight, and then snipping the suture off close to the single hitch 64 or double hitch 66. The single hitch 64 or double hitch 66 can be used to attach the suturing ring 10, 10' to the valvar rim 60 to receive any type of mechanical or tissue heart valve mechanism. The single hitch 64 or double hitch 66 is relatively easier to accomplish and smaller in comparison to the traditionally used single or double square knots.

Figure 16:
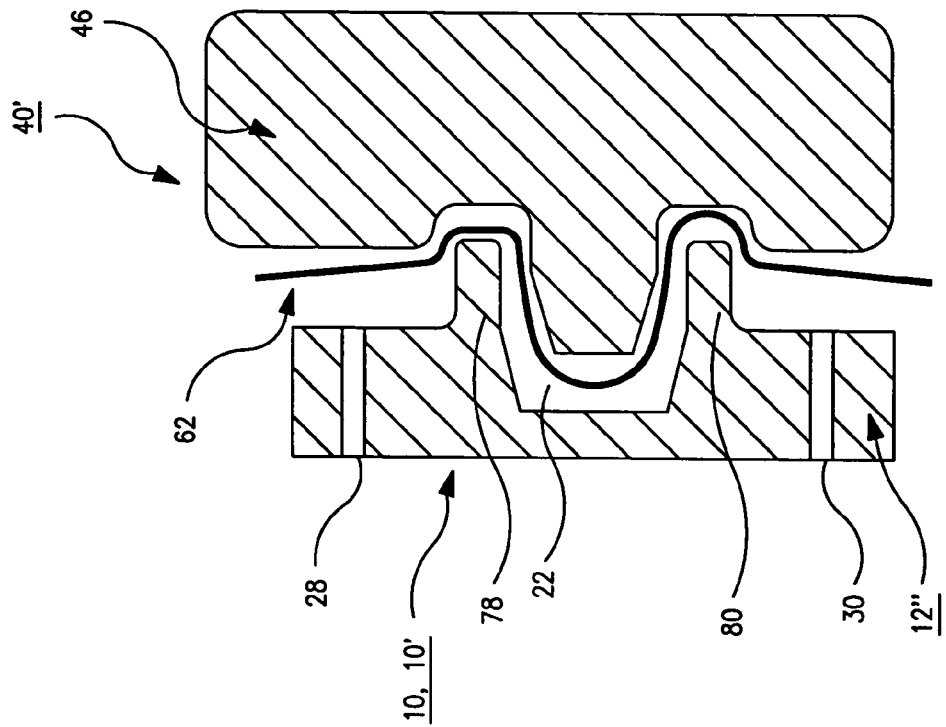
FIG. 16 is a still further cross-section view taken along lines 13-13 of FIG. 12 illustrating alternative configurations of the inner wall of the split stiffening band and the outer wall of the stent facilitating the entrapment of a suture between the inner wall of the suturing ring and the outer wall of the stent.
Figure 15:
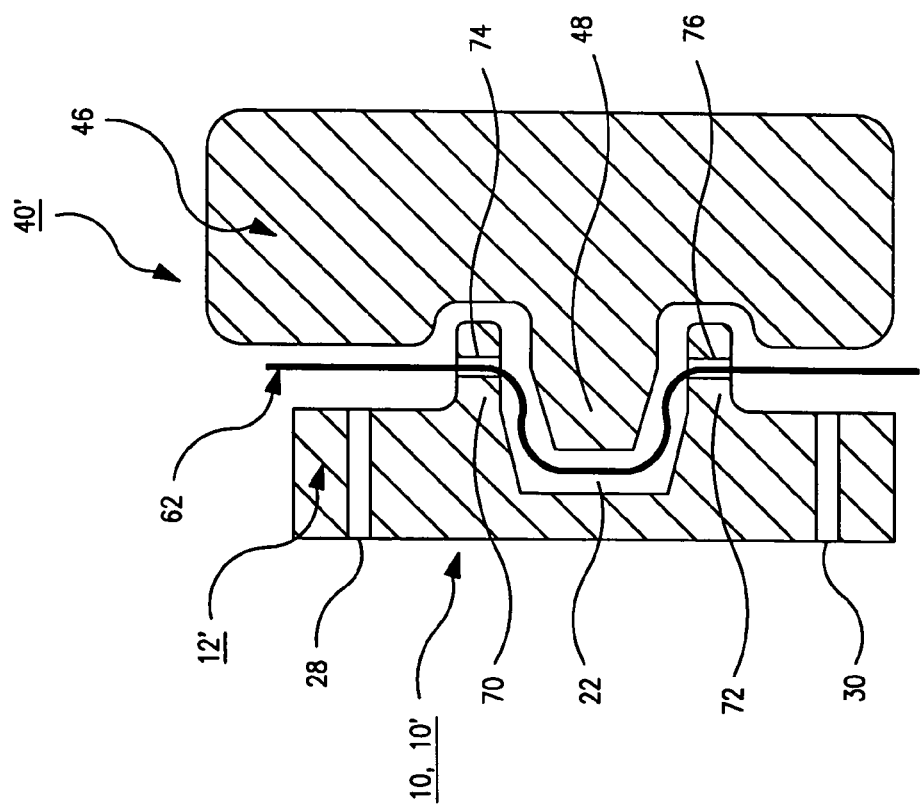
FIG. 15 is a further cross-section view taken along lines 13-13 of FIG. 12 illustrating alternative configurations of the inner wall of the split stiffening band and the outer wall of the stent facilitating the entrapment of a suture between the inner wall of the suturing ring and the outer wall of the stent.

Further implementations of the suture guides of this second aspect of the invention are illustrated in FIGS. 15 and 16, wherein the suturing ring fabric 32 and stent fabric 44 are not shown for convenience of illustration. In these embodiments, the routing of each suture 62 is accomplished using suture guides supported by or formed in the interior band sidewall 18. For example, a modified split stiffening band 12' is employed having a pair of flanges 70 and 72 extending inward above and below the groove 22 that fit on either side of the stent flange 48. A plurality of axially aligned pairs of suture guides or holes 74 and 76 are formed through the band flanges 70 and 72, respectively arrayed about the circumference of the split stiffening band 12'. One or more suture 62 can be extended through each axially aligned pair of suture holes 74, 76 and across the intervening groove 22. The sutures 62 can be employed to suture the suturing ring to the valvar rim 60 as shown in FIGS. 11 and 12 and are then entrapped within the groove 22 by the stent flange 48 when the band split ends 14 and 16 are restrained.

Furthermore, the band flanges 70 and 72 are preferably notched or slotted from the suture holes 74, 76 to the flange edges to enable the one or more suture 62 to be laterally, rather than axially, inserted into the axially aligned suture holes 74, 76. The split stiffening band 12 is flexible enough that the band split ends 14 and 16 can be separated apart to widen the slots or notches enough to pass the suture laterally into the axially aligned suture holes 74, 76 whereupon the slots or notches would then narrow upon release of the separation force.

The axially aligned suture holes are not employed in the further alternative split stiffening band 12" depicted in FIG. 16. Instead, the illustrated convoluted or circuitous path of each suture 62 around the stent flange 48 and the band flanges 70 and 72 and optionally through an upper suture slot 28 increases the resistance to release of each suture 62.

In these ways, the suturing of the suturing ring to the valvar rim is greatly simplified, resulting in fewer and smaller sized knots being required. Tissue ingrowth into the interstices of the suturing ring fabric occurs in time, and the sutures may become unnecessary to retain the suturing ring 10 in place. The single hitch 64 or double hitch 66 is expected to be sufficient to hold the suturing ring 10, 10' in place during the removal of a dysfunctional heart valve mechanism and replacement with a new heart valve mechanism.

Figure 17:
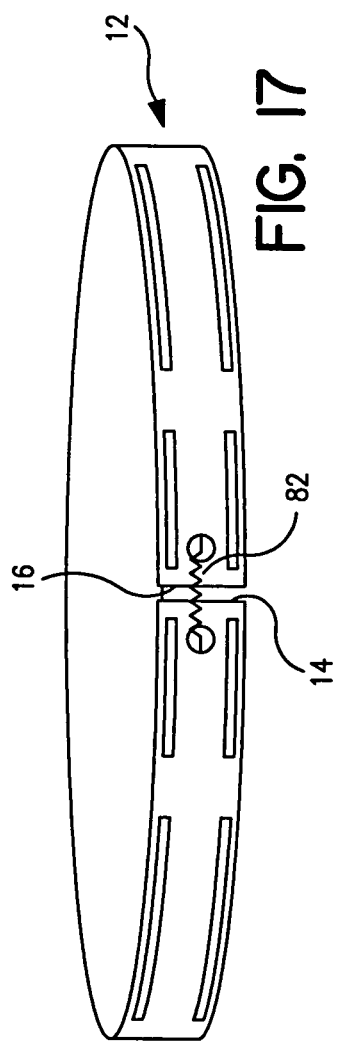
FIGS. 17-19 are plan schematic views of the split stiffening band illustrating an alternative or additional restraint mechanism for closing and opening the split stiffening band.
Figure 18:
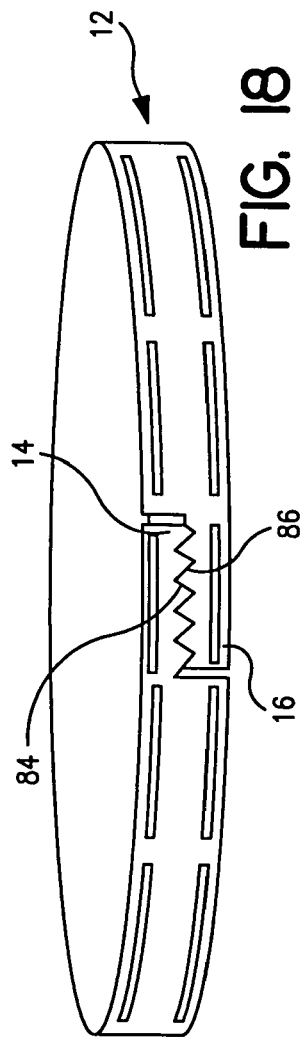
Figure 19:
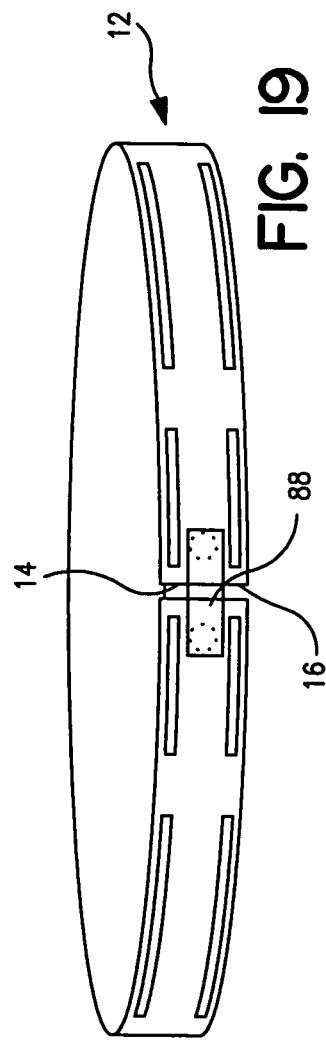

FIGS. 17-19 illustrate alternative or additional restraint mechanisms incorporated into the split stiffening band 12 for closing and opening the split stiffening band 12. At least the restraint mechanisms depicted in FIGS. 17 and 18 can be enclosed within the suturing ring fabric sewn together as illustrated by suturing ring 10 of FIG. 1 or exposed at the ends of the suturing ring fabric as illustrated by the suturing ring 10' of FIGS. 6 and 7.

In FIG. 17, a spring 82 is integrally formed to extend between the band split ends 14 and 16 maintaining the first annulus diameter AD1. The split band ends 14 and 16 can be separated apart to the increased second annulus diameter AD2 through application of force overcoming the spring tension to receive or remove a valve frame. The spring force then brings the split band ends 14 and 16 together when the force is removed. The spring force retains the valve frame seated within the suturing ring annulus and any of the sutures 62 inserted between the valve frame and the suturing ring as described above.

In FIG. 18, the band split ends 14 and 16 are modified to have longitudinally extending mating teeth or hooks 84 and 86 that are normally interlocked to prevent spreading apart of the band split ends 14 and 16 and provide the first annulus diameter AD1. Opposed axial forces can be applied to release and then set the mating teeth or hooks 84 and 86 together to expand the annulus diameter to the second annulus diameter AD2 to receive or remove a valve frame. Force can then be applied longitudinally to reset the mating teeth or hooks 84 and 86 and brings the split band ends 14 and 16 back closer together. The mating teeth or hooks 84 and 86 retain the valve frame seated within the suturing ring annulus and any of the sutures 62 inserted between the valve frame and the suturing ring as described above.

In FIG. 19, the band split ends 14 and 16 are modified to have a longitudinally extending restraint band 88 having snaps or buttons that are received in the suture holes 34 and 36 to prevent spreading apart of the band split ends 14 and 16 and provide the first annulus diameter AD1. One of the snaps or buttons can be released from one of the suture holes 34 and 36 by use of a forceps or the like to expand the annulus diameter to the second annulus diameter AD2 to receive or remove a valve frame. The snaps or buttons can then be reapplied to retrain the split band ends 14 and 16 back closer together. The restraint band retains the valve frame seated within the suturing ring annulus and any of the sutures 62 inserted between the valve frame and the suturing ring as described above.

Figure 20:
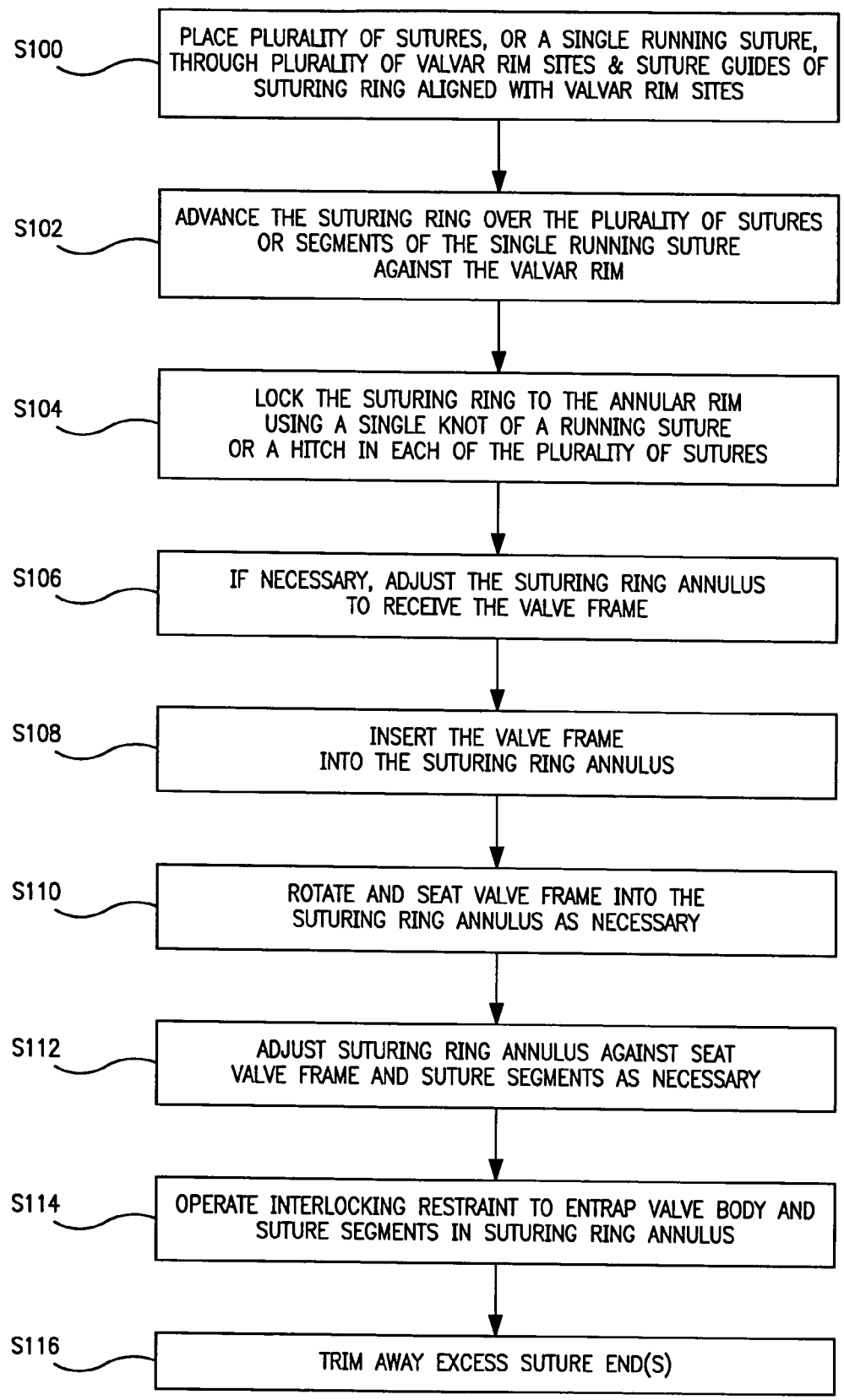
FIG. 20 is a flow chart illustrating one preferred embodiment of initially implanting a suturing ring and heart valve mechanism to form a heart valve prosthesis in accordance with the present invention.

A preferred method incorporating both aspects of the invention of surgical implantation of the suturing rings 10, 10' of the present invention and fixation of a tissue valve stent 40 or a mechanical valve body 50 into the suturing ring annulus is depicted in FIG. 20. In this method, the suturing ring 10, 10' is first surgically implanted in steps S100-S104 to the prepared valvar rim. The surgeon can either use a plurality of sutures 62 fitted through each one or adjacent pairs of the above-described suture guides or a single running suture fitted through all of the suture guides. The danger that the single running suture may break during chronic implantation and cause the suturing ring 10, 10' to loosen from the valvar rim 60 is overcome because multiple parallel segments of the single running suture are entrapped between the stiffening ring 12 and the valve frame 40 or 50 that would remain firmly attached to the valvar rim 60.

Preferably, in either case, the suture(s) 62 are sewn through a suture guide, then inferiorly through a site of the valvar rim that the suture guide will be aligned with, then back superiorly through a site of the valvar rim that the adjacent suture guide is aligned with, and then through the adjacent suture guide in step S100. The suturing is facilitated because the surgeon's view of the sites of the valvar rim is not obstructed by any valve structure. In addition, the surgeon can extend instruments or a finger through the empty suturing ring annulus to effect sewing the suture(s) through the sites of the valvar rim 60 to speed the process and avoid damage to the valvar rim that could other wise occur.

Figure 22:
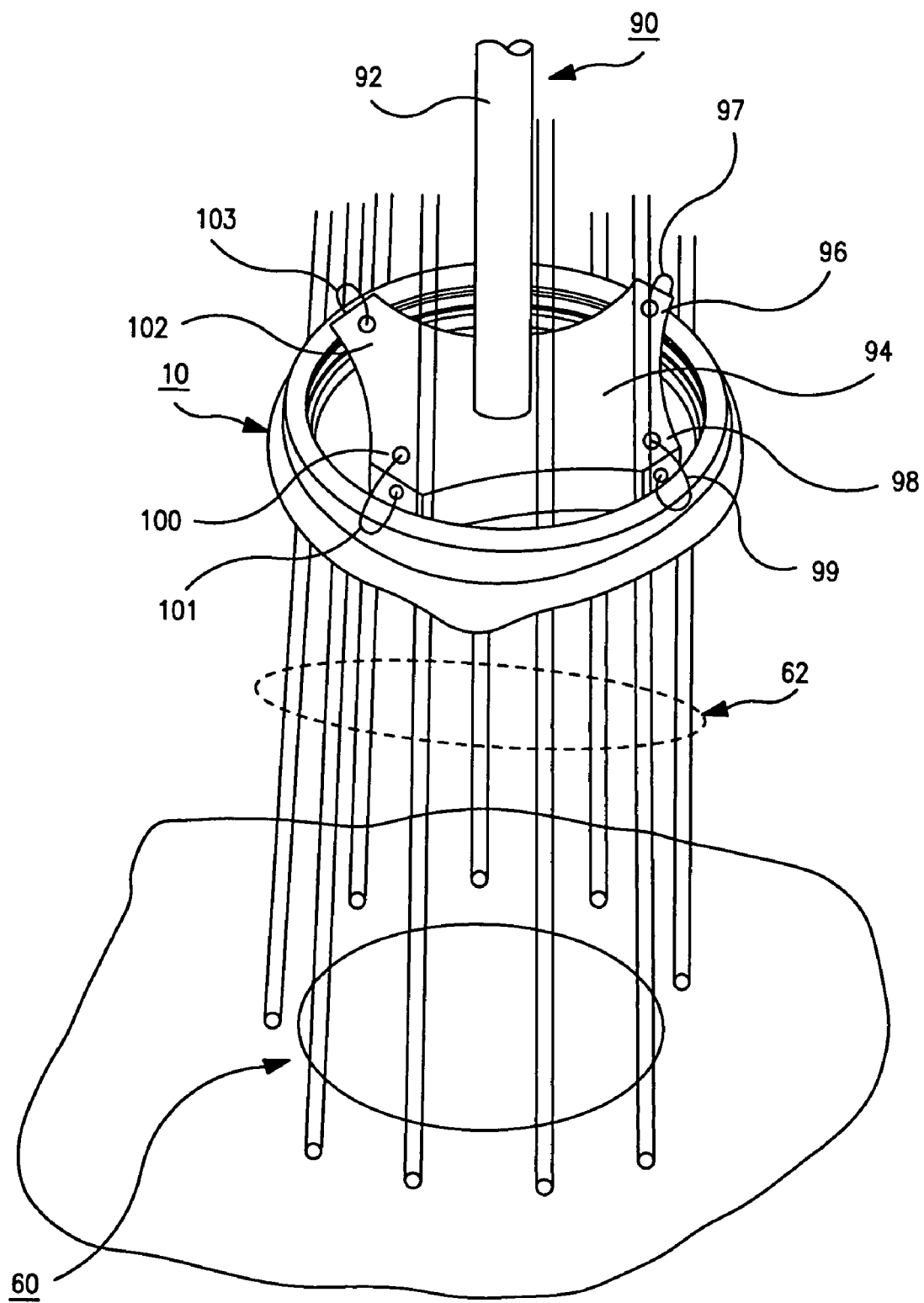
FIG. 22 is a perspective schematic view of a suture ring holder engaging the suturing ring by severable sutures to enable positioning and suturing of the suturing ring to the valvar rim.

The suturing ring 10, 10' can be suspended on taut suture(s) 62 in alignment with valvar rim 60 as shown in FIG. 11 and advanced against the valvar rim 60 over the taut suture(s) in step S102. One way of holding the suturing ring 10, 10' using a tool 90 is depicted in FIG. 22. Tool 90 is formed of an elongated handle 92 attached to a spanner 94 having a plurality of arms, e.g., arms 96, 98, 100, 102, that extend to the suturing ring annulus and are sutured to the stiffening ring 10, 10' by tool sutures 97, 99, 101 and 103. The stiffening band and the arms 96, 98, 100, 102 are formed with special suture holes that tool sutures 97, 99, 101 and 103 extend through and tied. The tool sutures 97, 99, 101 and 103 are adapted to be cut when the suturing ring 10, 10' is snugged up against the valvar rim 60.

The suturing ring 10, 10' is snugged up against and locked to the valvar rim 60 by tying a knot in the single running suture or knotting the ends of the individual sutures 62 in step 104. Preferably, the suture(s) 62 are inserted through the upper suture slots 28 as shown in the examples of FIGS. 13 and 14, and the single or double slip hitch 64 or 66 is formed in the turns of the suture extending over the suturing ring fabric 34. Slip hitches are easier to form by the surgeon using instruments than a square knot.

The suturing ring annulus is adjusted as necessary in step S106 so that the valve frame 40 or 50 is then inserted into it. For example, the gap G can be widened as necessary to receive the flange 48 within the slot 22 or to fit the suturing ring 10, 10' into the U-shaped channel of the mechanical valve body 50 as described above. The valve frame 40 or 50 is inserted into, rotated and seated in steps S108, S110, and S112 in the ways described above.

Figure 23:
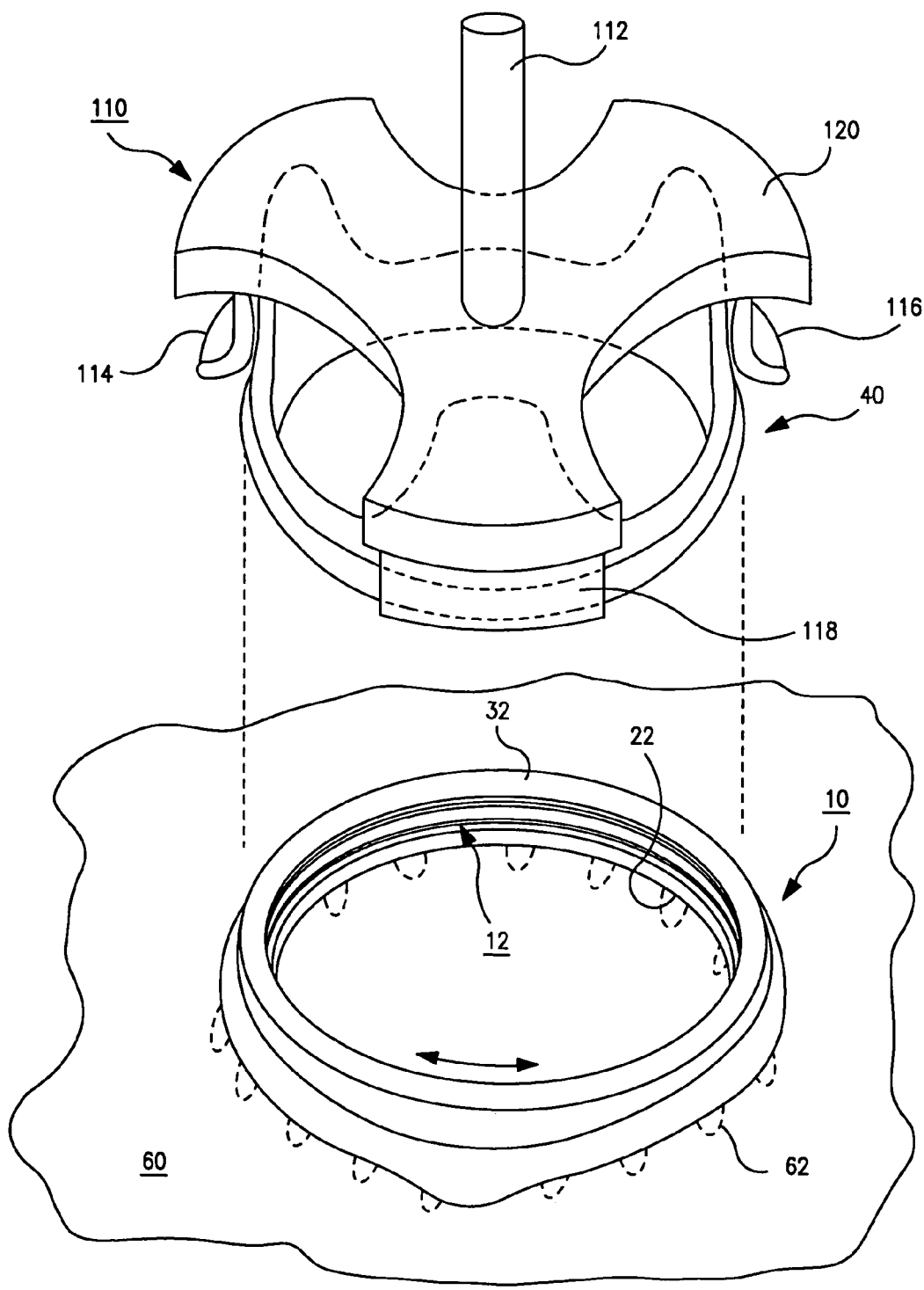
FIG. 23 is a perspective schematic view of a stent holder engaging the stent frictionally or by severable sutures to enable positioning of the stent into the suturing ring.

The valve mechanism is preferably mounted to a valve holder tool as it is inserted into and seated in the suturing ring annulus. For example, a stent holder 110 is illustrated in FIG. 23 comprising a stent holder handle 112 attached to a stent holder spanner 120 having three fingers 114, 116 and 118 that extend over and against the stent struts and thereby frictionally engage the stent 40. A suture may also be placed around or through holes in the three fingers 114, 116 and 118 and the corresponding stent struts to hold the stent 40. The stent holder 110 is manipulated to insert the stent 40 into the sewing ring annulus in step S108. The lengths of the three fingers 114, 116, 118 are selected so that the outwardly ending free ends of the three fingers 114, 116, 118 bear against the suturing ring 10, 10' when the stent flange is positioned to be seated in the groove of the stiffening ring as described above. The outwardly ending free ends of the three fingers 114, 116, 118 bearing against the suturing ring 10, 10' when the stent flange is properly seated in the groove of the stiffening ring 10. 10' prevent the surgeon from extending the stent 40 all the way through the suturing ring annulus.

The interlocking restraint of one of the above-described types is operated in step S114. Preferably, the interlocking restraint is the above-described suture 38, and that is sewn through the suture holes 34 and 36, drawn tight, and either tied or thermally welded against the suturing ring fabric in step S114.

The excess suture length of the running suture or lengths of the separate sutures 62 are then trimmed in step S116. Advantageously, tightened slip hitches 64 or 66 are small in size and will remain in place when a replacement surgical procedure of the types described above are undertaken.

The various aspects of the suturing ring 10, 10' of the present invention employing any of the interlocking restraints presents the surgeon with a wide range of possible ways of surgically implanting it upon or against the valvar rim 60. The suturing ring 10, 10' of the present invention can be supplied with the outwardly extending collar to enable traditional suturing through it as depicted in FIGS. 1, 8 and 9. However, the surgeon can ignore the suturing ring fabric collar and follow any of the above-described techniques, e.g., steps S100-S104 to entrap segments of the suture(s) 62 between the valve frame and the suturing ring annulus.

It is desirable in many instances to implant a heart valve prosthesis in or to a valvar rim 60 having as large a valve annulus as possible to enable maximal unobstructed blood flow through it when the occluder is not seated. Advantageously, a larger diameter suturing ring 10, 10' (accommodating a larger diameter valve mechanism and valve annulus) can be selected to fit the valvar rim if the surgeon follows any of the above-described techniques, e.g., steps S100-S104 to entrap segments of the suture(s) 62 between the valve frame and the suturing ring annulus rather than suturing through the fabric collar. Models of suturing ring 10, 10' can be provided with a minimal sized outwardly extending collar of the suturing ring fabric 32 and a relatively larger suturing ring annulus for selection by a surgeon intending to follow any of the above-described techniques, e.g., steps S100-S104 to entrap segments of the suture(s) 62 between the valve frame and the suturing ring annulus.

Figure 21:
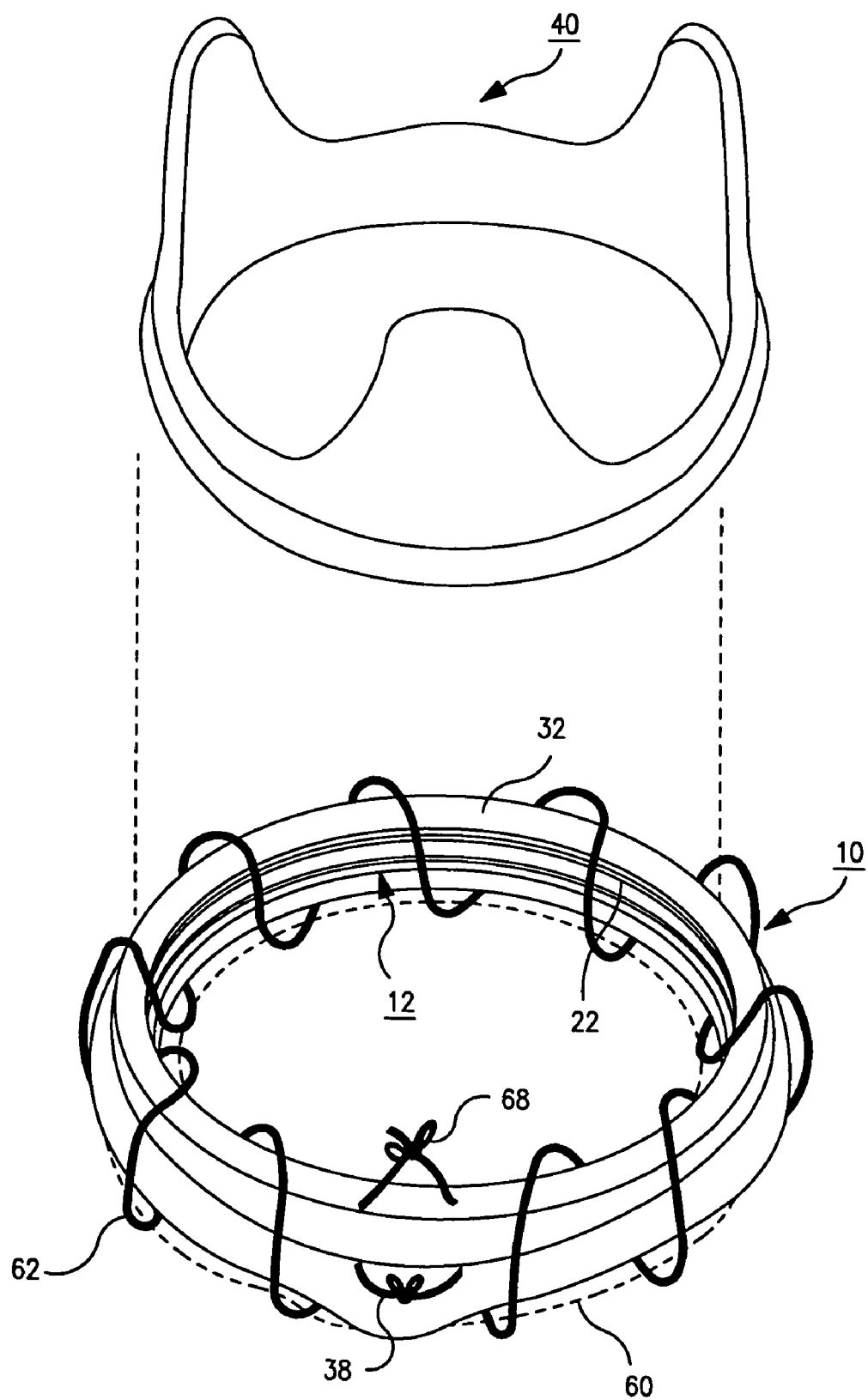
FIG. 21 is a perspective view of a stent arranged to be inserted into the annulus of a suturing ring of the present invention sutured by a single running suture to a valvar rim.

All of the above described methods of initially implanting the suturing ring 10, 10' are facilitated by having the ability to see through, extend the surgeon's finger or instruments through and extend sutures through the open suturing ring annulus. A further simplified way of suturing the suturing ring 10, 10' to a valvar rim 60 (which in practice may simply be the tubular valvar annulus remaining after surgical excision of the native heart valve) employing a single suture 62 is depicted in FIG. 21. This method, the suturing ring 10, 10' is held within or against the valvar annulus constituting the valvar rim 60 by a suitable instrument. A number of loops of the suture 62 are made by the surgeon extending entirely around the suturing ring 10, 10' via the open suturing ring annulus and through adjoining valvar tissue under or within valvar rim 60. The suture ends can be drawn through any selected adjacent pair of any of the suture holes 28, 30, 34, 36 depicted in FIG. 5 and/or just through the suturing ring fabric 32. The suture 62 is pulled taut, the suture ends are tied together in a suture knot 68, and the excess suture is trimmed away. In this way, the surgeon can implant the maximum diameter suturing ring 10, 10' in a tubular valvar annulus that is otherwise difficult sized only a single knot 68 is necessary. Of course, it would also be possible to form separate hitches in the suture ends as described above with respect to FIGS. 13 and 14.

Then, steps S106-S116 of FIG. 20 are followed to affix the valve mechanism in place. The suture segments are entrapped between the suturing ring annulus and the valve frame as described above. These entrapped segments of the suture 62 still hold the suturing ring 10, 10' in place even if the suture 62 happens to break at any point along its length.

The surgical steps of replacing a tissue valve or mechanical valve at a later time are greatly simplified by the present invention. All that is necessary to do is to: 1) Surgically expose the chronically implanted valve mechanism and suturing ring assembly and clean the tissue overgrowth away; 2) Locate the suturing ring restraint; 3) Release the restraint; 4) Insert a scalpel or a blunt probe into the interface between the split ring and the valve frame starting from the split end, 5) Gently peel the split ring from the valve frame along the circumferential direction using the same instrument, 6) Remove the valve mechanism from the annulus of the suturing ring; 7) Insert and seat the new replacement valve mechanism into the annulus; 8) Attach the replacement valve mechanism therein following any of the above-described techniques depending upon the particular design of the suturing ring and the replacement valve mechanism; and 9) Complete the surgical closure.

As noted above, the restraint can be a suture sewed through the suturing ring fabric and suture holes adjacent the split ends of the stiffening ring. The suture can be identified at the bunched fabric that the suture is sewn through. The fabric can be marked or colored to indicate where the suture is located to be cut in step 3), and a new suture is to be sewn in the attachment in step 8). If the alternative restraints illustrated in FIGS. 17-19 are employed, then they are opened in step 3) and closed in step 8).

Advantageously, this process allows the dysfunctional valve mechanism to be replaced by the same or a different type of valve mechanism that can be seated into the annulus of the suturing ring in step 7). However, the chronically sewn-in suturing ring can also be used as a docking station for an incompatibly dimensioned heart valve prosthesis comprising a tissue or mechanical heart mechanism that is supplied with an integral suturing ring. In this case, step 8) can be replaced by placing the integral valve suturing ring within or onto the annulus of the chronically sewn-in suturing ring and suturing them together.

Figure 24A:
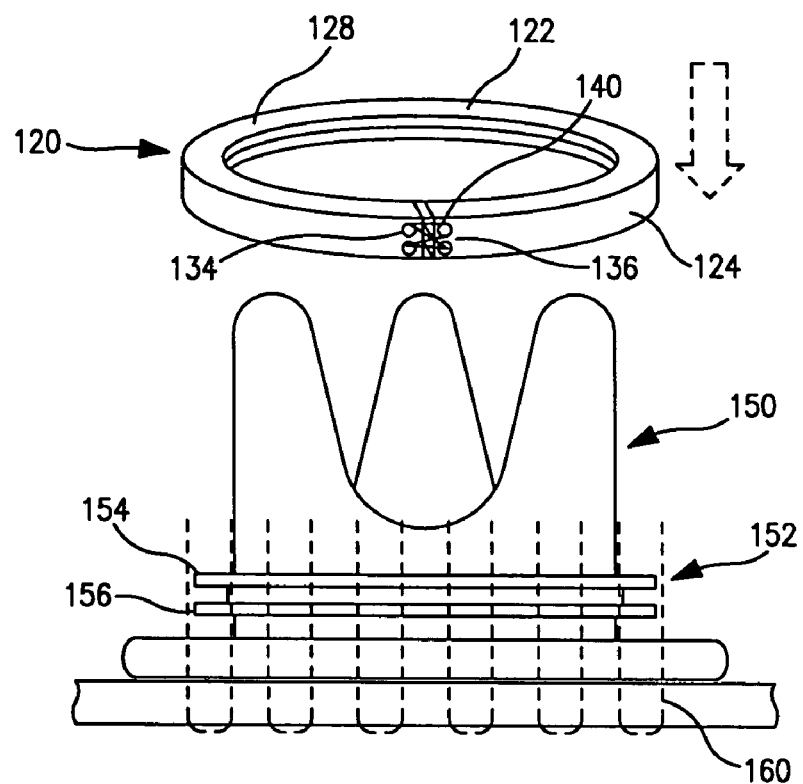
FIGS. 24a-b are plan schematic views of one embodiment in which a band engages a circumferential frame portion on a valve body in order to capture sutures securing the valve to a valvar rim.
Figure 24B:
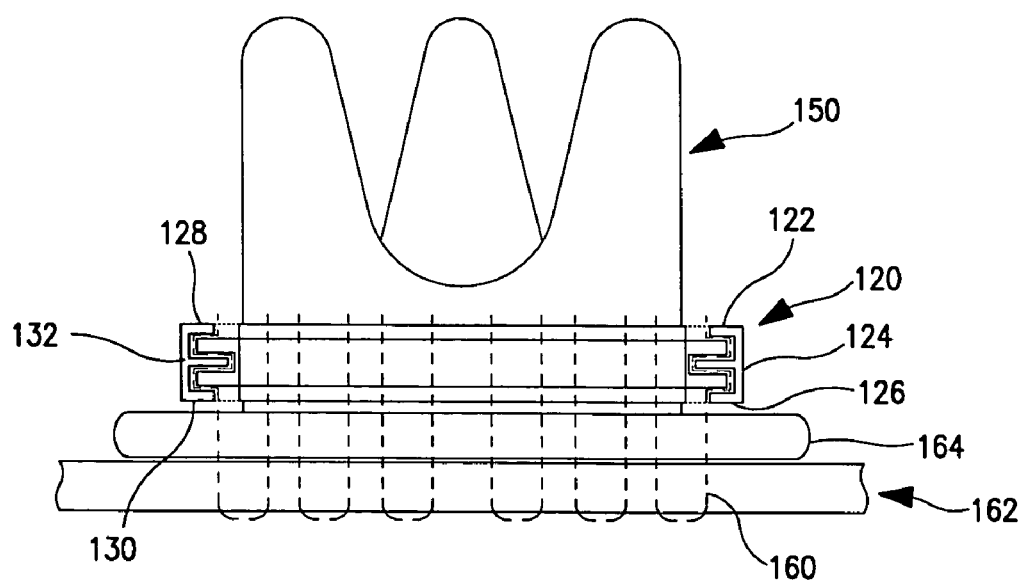

Referring now to FIGS. 24a-b, in yet another embodiment of the invention, a band 120 is applied to a valve having a suturing ring in order to secure sutures in place. The band 120 has substantially the same properties as the band 12 discussed previously. Band 120 has a top portion 122, an outside portion 124, and a bottom portion 126. The top portion 122 and bottom portion 126 include inwardly extending circumferential flanges 128, 130 respectively. Centrally located on the band 120 is a third inwardly extending circumferential flange 132 that is longer than the other flanges 128, 130. The band includes split ends 134, 136, which are secured together by a restraint mechanism such as a suture 140 that is capable of locking the position of the split ends 134, 136. The suture 140 or other restraint mechanism is preferable made from a resilient material such as nitinol, which can be pseudoelastically deformed to open the band 120 and then released to return it to an undeformed condition, thereby closing the band 120 by pulling the split ends 134, 136 together. Alternatively, a nitinol restraint mechanism can be used as a shape memory device in which the restraint mechanism responds to warming to body temperature by transforming the restraint from its martensitic state to its austenitic state. Such a phase transformation can pull the split ends 134, 136 together as the device is warmed. Other restraint mechanisms can be used as well, but most preferably the selected restraint mechanism permits the surgeon implanting the device to remove or loosen the restraint mechanism if the band 120 must be removed, released or repositioned.

Valve 150 can be a mechanical or tissue valve having a frame or stent. Valve 150 is shown to be a tissue valve having a frame portion 152 that includes a first, outwardly-extending circumferential flange 154 at the top of the frame portion 152 and a second, outwardly-extending circumferential flange 156 at the bottom of the frame portion 152. As shown in FIG. 24b, the flanges 154, 156 are sized to fit within recesses in the band 120 between inwardly extending flanges 128, 130, 132 and are spaced apart to permit the centrally located flange 132 to reside between the flanges 154, 156. The band 120 and frame portion 152 thereby cooperate to form an interlocking engagement that can engage and restrain the movement of a suture 160 that may be introduced and secured between them. It will be appreciated that many other configurations of interlocking elements can be used to engage and restrain the movement of a suture. Preferably, such interlocking elements are characterized by a tortuous path for the suture and closely mating surfaces between the band 120 and the frame portion 152.

In operation, the valve 150 is secured by a plurality of sutures 160 to a prepared valvar rim 162 by bringing the sutures through a suture ring 164, through a portion of the valvar rim 162 and returning the suture through the suture ring 164. The ends of the sutures 160 extending away from the valvar rim 162 preferably run through the suture ring 164 at points near the outer portion of the frame portion 152. When all of the sutures 160 have been positioned, the suture ring 164 is pressed against the valvar rim 162 and the sutures 160 are drawn away from the suturing ring 164 to take up any slack. The band 120 is then placed over the valve 150 and advanced into position over the frame portion 152. In order to permit the band 120 to achieve a mating engagement with the frame portion 152, the split ends 134, 136 are spaced apart sufficiently to permit the inwardly extending flanges 130, 132 to clear outwardly extending flanges 154, 156. The split ends 134, 136 may be brought to the spaced apart position by prying them apart slightly, if that is necessary. The restraint mechanism such as the suture 140 is preferably affixed to the split ends 134, 136 prior to the time the band 120 is placed over the frame portion 152. If the restraint mechanism is a resilient restraint, such as a spring, the restraint can be in place as the split ends 134, 136 are brought to a spaced apart position and then simply released. Alternatively, a nitinol restraint can be allowed to warm to body temperature to pull the split ends 134, 136 together. In yet another way, a restraint mechanism such as a suture 140 can be loosely positioned in apertures on the spilt ends 134, 136 and can be brought from an unsecured state to a taut, secured state by the surgeon after the band 120 is placed over the frame portion 152. If desired, a suitable ring-spreading tool such as those known in the art can be used to facilitate the correct positioning of the split ends 134, 136. Once the band is in a mating position with the frame portion 152, the split ends 134, 136 can be drawn together in order to urge the flanges 128, 130, 132 of the band 120 into contact with the sutures 160 and to drive the sutures 160 into the recesses in the frame portion 152 defined by the flanges 154, 156 and into recesses defined in the band 120 by the flanges 128, 130, 132. The band 120 then secures the sutures 160 from movement and excess suture material extending above the top portion 122 of the band may be removed. In order to facilitate a rapid surgical procedure, the sutures so secured between the band 120 and the frame portion 152 are secured entirely by the band 120 and frame portion 152 without the need to tie any knots in the sutures 160. If the surgeon finds it necessary to tighten any of the sutures 160 after the band 120 is secured over the frame portion 152, the split ends 134, 136 can be drawn apart until the sutures to be tightened are moveable. The sutures 160 can then be pulled tight and the band 120 drawn against the frame portion 152 to resecure the sutures 160.

Figure 25A:
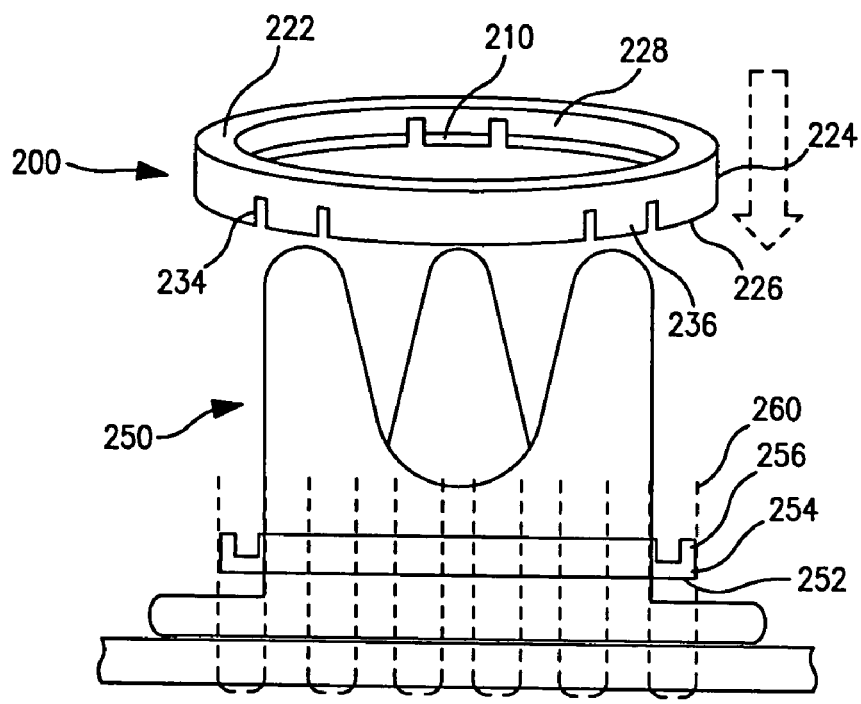
FIGS. 25a-b are plan schematic views of another embodiment in which a band engages a circumferential frame portion on a valve body in order to capture sutures securing the valve to a valvar rim.
Figure 25B:
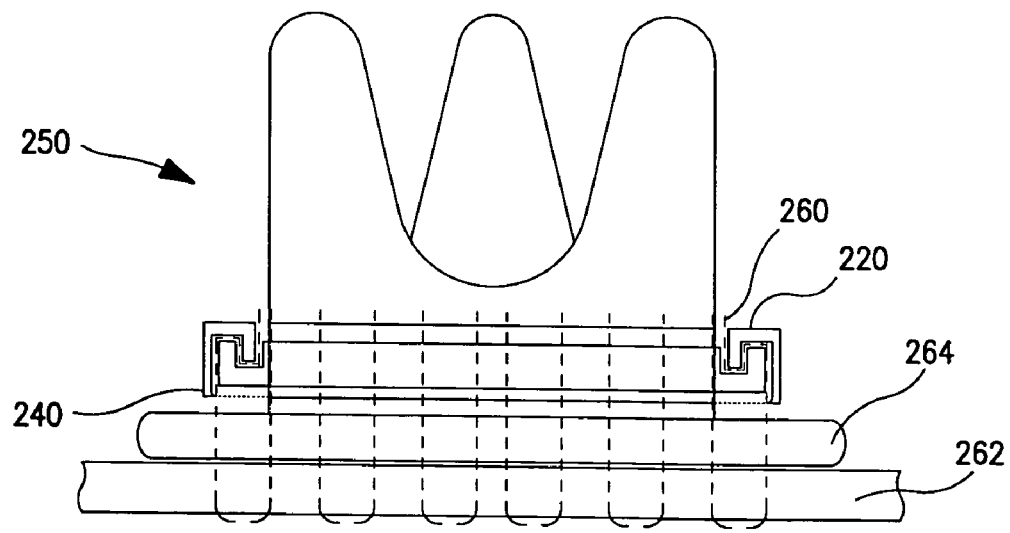
Figure 26A:
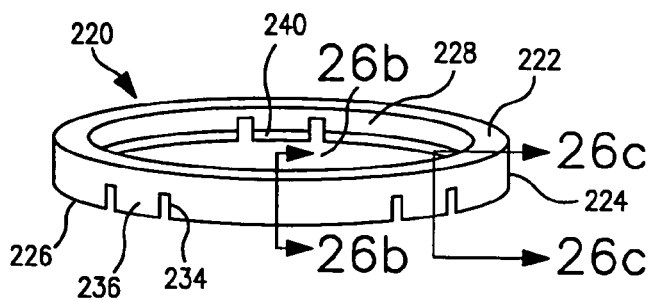
Figure 26B:
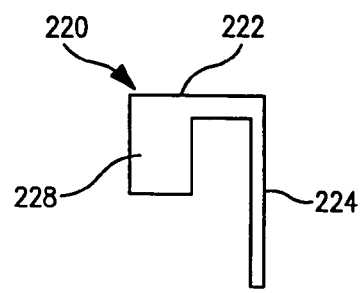
FIG. 26b is a cross sectional view of the band of FIG. 26a taken along the line 26b-26b.
Figure 26C:
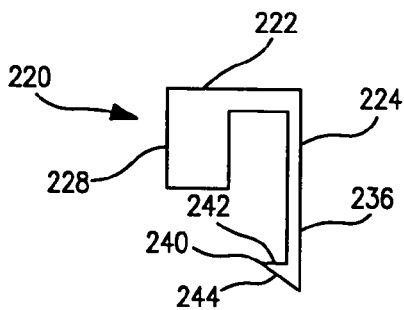
FIG. 26c is a cross sectional view of the band of FIG. 26a taken along the line 26c-26c.
Figure 26D:
Figure 26E:
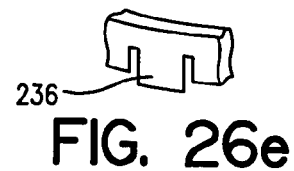
FIG. 26e is a partial perspective view of yet another embodiment of a band similar to that shown in FIG. 26a FIG. 27a is a cross sectional view of the band and frame portion of FIG. 25a moving into engagement.

Referring now to FIGS. 25a-b and FIGS. 26a-e, in yet another embodiment of the invention, a band 220 is also applied to a valve having a suturing ring in order to secure sutures in place. Band 220 is made in a closed ring configuration with a top portion 222 joined at an outside edge to an outside portion 224. The top portion 222 comprises an inwardly extending flange that also joins at an inner edge with a downwardly extending circumferential flange 228. The band 220 includes a plurality of splits 234 that extend through the outside portion 224 from a bottom edge 226 upward to a central portion of the outside portion 224. The splits 234 do not extend completely through the band 220. The splits 234 are preferably spaced around the circumference of the band 220 such that pairs of adjoining splits create tab portions 236 around the circumference of the band 220. The tab portions 236 can also extend partially below the bottom edge 226 of the ring as in FIG. 26e. Also, the tab portions 236 may be made independent of any splits as shown in FIG. 26d where the tab portions 236 are shown protruding below the bottom edge 226. A barbed portion 240 is on the lower edge of each of the tab portions 236, as best appreciated in cross-section in FIG. 26c. The barbed portions 240 include a substantially flat upper portion 242 and an angled lower portion 244. The upper portion 242 can have a longitudinal axis that optionally projects perpendicular to the tab portion 236. Portions of the band 220 between the tab portions 236 can be formed without a barbed portion as shown in FIG. 26b. The tab portions are designed so that they may be resiliently spread radially outwardly at the lower, barbed portion 240 and then released to return them to an unspread position. The tab portions 236 can, by their resilient deformation, form a locking mechanism with a complimentary structure on a frame portion 252 of a valve 250 in a locking fit. Locking mechanisms employing structures other than a barb shape can also be used so long as they provide a positive, locking attachment between the band 220 and the frame portion 252. Preferably, multiple tabs are used on the band 220 and are spaced around the circumference of the band 220 in order to provide an even locking attachment between the band 220 and frame portion. Two or more such tabs are preferred.

Figure 27A:
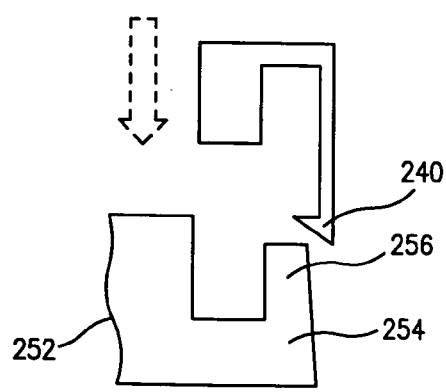
FIG. 27b is a cross sectional view of the band and frame portion of FIG. 27a in an engaged and locked position.
Figure 27B:
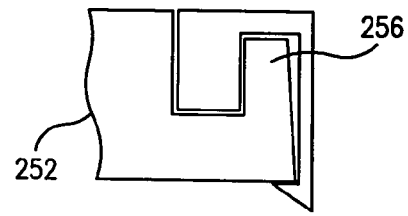
Figure 28A:
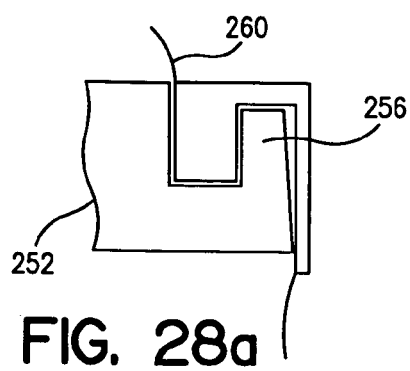
Figure 28B:
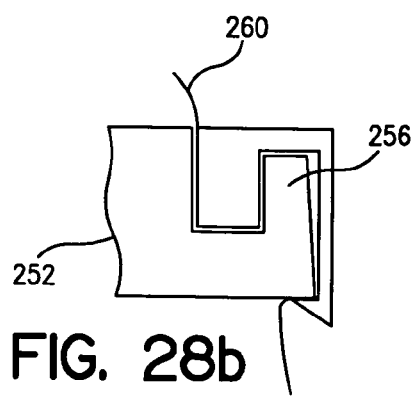

Referring now to FIGS. 25a-b and FIGS. 27a-b, valve 250 can be a mechanical or tissue valve having a frame or stent. Valve 250 is shown to be a tissue valve having the frame portion 252 that includes a first, outwardly-extending circumferential flange 254 with an upwardly extending portion 256 that forms a circumferential recess in the flange. The recess is therefore open in the outflow side of the valve. As shown in FIG. 25b and FIGS. 27a-b, the flange 254 and upwardly extending portion 256 are sized to fit within the recess in the band 220 while the downwardly extending flange 228 of the band is sized to fit within the recess in the flange 254. Preferably, the upwardly extending portion 256 is tapered slightly on its outer edge such that the tab portion 236 will be deflected outwardly by contact with the taper. The band 220 and frame portion 252 thereby cooperate to form an interlocking engagement in which the barb portion 240 catches on a portion of the frame portion 252 and holds the band 220 and frame portion together. As shown in FIG. 25b and FIG. 28a, the mating of the frame portion 252 and band 220 in this manner can prevent movement of a suture 260 that may be introduced and secured between them. Because the barb portion 240 has an angled lower portion 244, and because of the taper on the upward extending portion 256 the placement of the band on the flange is a simple press fit. That is, the band 220 can be readily pressed onto the flange 254 by a straight downward motion that deflects the tab portions 240 simultaneously and causes them to lock simultaneously in a locking fit onto a complementary structure on the flange 254. In the embodiment shown, the barb portion engages the inflow side of the flange 254. It will be appreciated that many other configurations of the locking mechanism can be used, including placing the locking barbs or elements on the flange rather than on the band and applying a band that has a complementary structure for locking the barbs to the band. Thus, a band without splits or tabs could be used according to the invention to engage and restrain the movement of a suture.

In operation, the valve 250 is secured by a plurality of sutures 260 to a prepared valvar rim 262 by bringing the sutures through a suture ring 264, through a portion of the valvar rim 262 and returning the suture through the suture ring 264. The ends of the sutures 260 extending away from the valvar rim 262 preferably run through the suture ring 264 at points near the outer portion of the frame portion 252. When all of the sutures 260 have been positioned, the suture ring 264 is pressed against the valvar rim 262 and the sutures 260 are drawn away from the suturing ring 264 to take up any slack. The band 220 is then placed over the valve 250 and advanced into position over the frame portion 252 and pressed onto the frame portion 252 until a locking fit is achieved between the barbs 240 and the frame portion 252. Preferably, the frame portion 252 is designed to provide a circumferentially cooperating portion that will receive the barbs 240 in any relative rotational orientation of the band 220. Alternatively, the frame portion could be provided with a mark or indicator that could be aligned with a similar mark or indicator on the band in order to align the components. If the surgeon finds it necessary to tighten any of the sutures 260 after the band 220 is secured over the frame portion 252, the tab portions 236 can be resiliently drawn away from the frame portion 252 so that the barbs 240 are released from engagement with the frame portion. The band 220 is then drawn upward until the sutures to be tightened are moveable. The sutures 260 can then be pulled tight and the band 220 can again be pressed against the frame portion 252 to resecure the sutures 260.

Figure 29D:
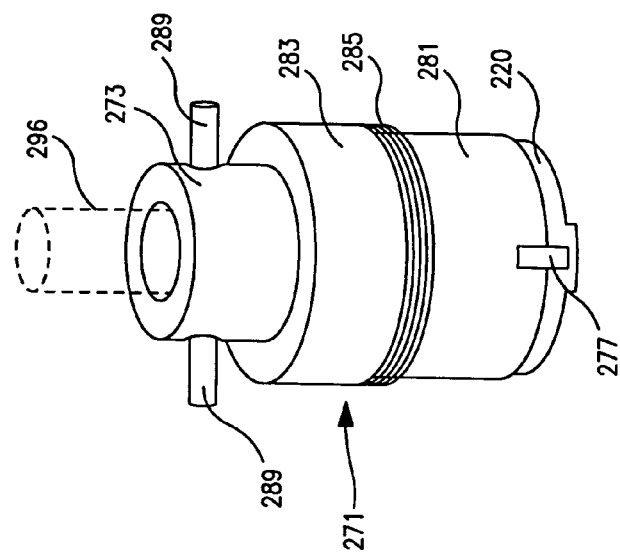
FIG. 29d is a perspective view of the applicator tool of FIG. 29c engaged with a band
Figure 29C:
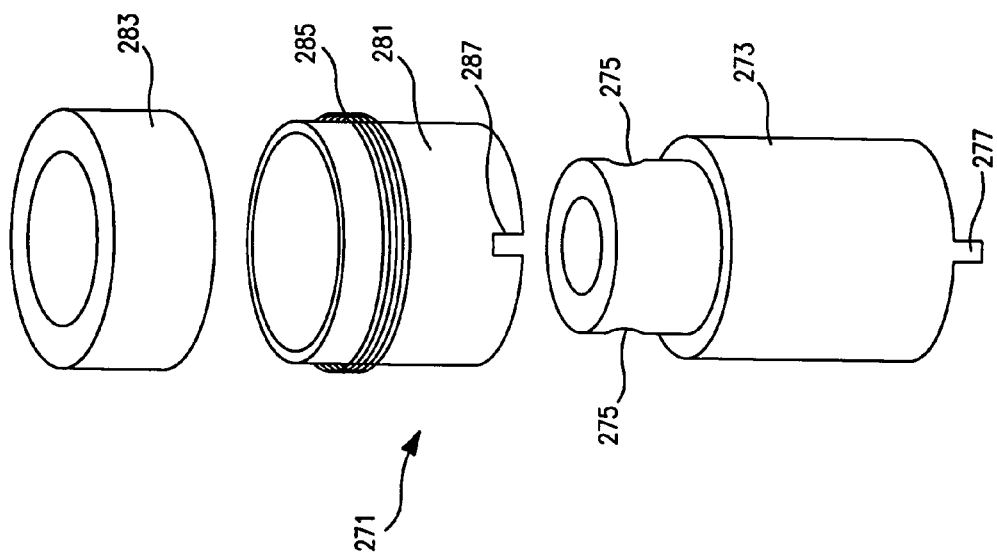
FIG. 29c is an exploded perspective view of an alternative band applicator tool.

The process for pressing the band 220 onto the frame portion 252 can be facilitated by using a pressing tool 270 as set forth in FIGS. 29a-b. The pressing tool 270 includes a cylindrical body 272 and a handle portion 280. The cylindrical body 272 includes a shoulder portion 274 that is configured to engage the band 220. The handle portion 280 includes a portion that is interior to the body 272 and a portion that is exterior to the body and is free to rotate with respect to the body 272 on threads 282 engaging complimentary threads on the body 272. The interior of the body 272 is sized to receive the valve and any valve holder and handle that may be attached to the valve during the surgical procedure. The interior portion of the handle portion is sized to engage with the valve and valve holder. In operation, the pressing tool 270 is placed over the valve and with the band engaged with the body 272 and in place against the frame portion 252, the body is manually rotated to advance the body 272 over the threads 282 relative to the handle 280. This advances the band 220 onto the frame portion 252 until the closure is achieved between the band 220 and frame portion 252. Alternatively, another pressing tool 271 can be used to facilitate positioning of the band 220 as shown in FIGS. 29c-d. A cylindrical body portion 273 includes retention tabs 277 that are configured to grip the band 220. Preferably three or more such tabs 277 are evenly spaced around the body 273 to grip the band 220 evenly at several places. Threaded apertures 275 are on an upper portion of the body 273 in order to permit the body to be secured to the handle of a valve holder by locking elements 289. A sleeve 281 has screw threads 285 on an outer portion thereof and a notch 287 configured to provide an opening for tab 277. The sleeve 281 fits over the body 273. A cap 283 configured to fit over an upper portion of body 273 includes internal screw threads (not shown) which are intended to mate with screw threads 285 on the sleeve 281. In operation, the tool 271 slides over the handle 296 of the valve holder and the locking elements 289 are screwed into locking engagement with the handle 296. The cap 283 is then manually rotated which causes the sleeve 281 to be advanced over the body 273. As the sleeve 281 is advanced, it contacts the band 220 and pushes the band 220 off of the retention tabs 277 and into engagement with the flange of the frame portion.

Figure 30A:
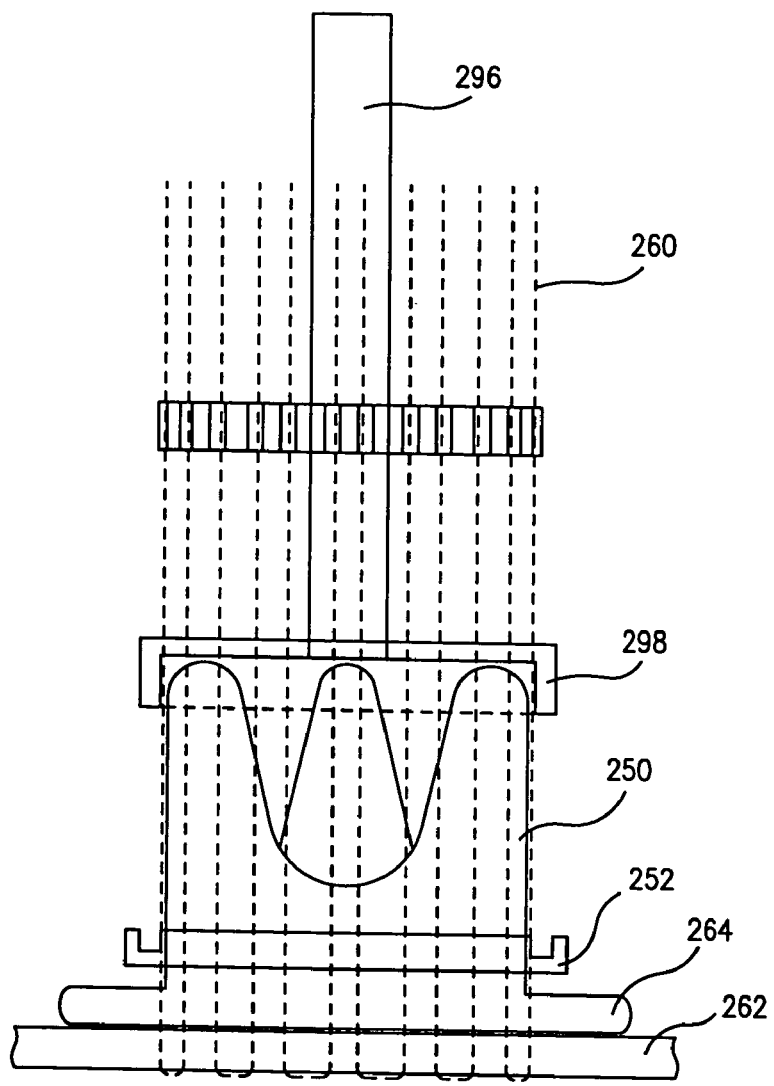
FIG. 30a is a plan schematic view of the valve of FIG. 25a including a valve holder tool and a suture tensioning tool.
Figure 30B:
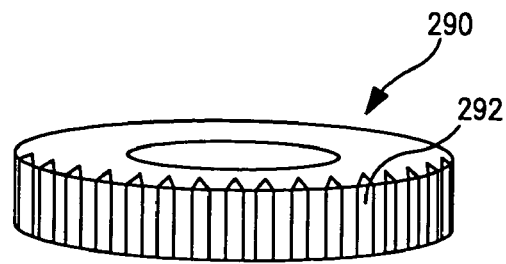
Figure 31:
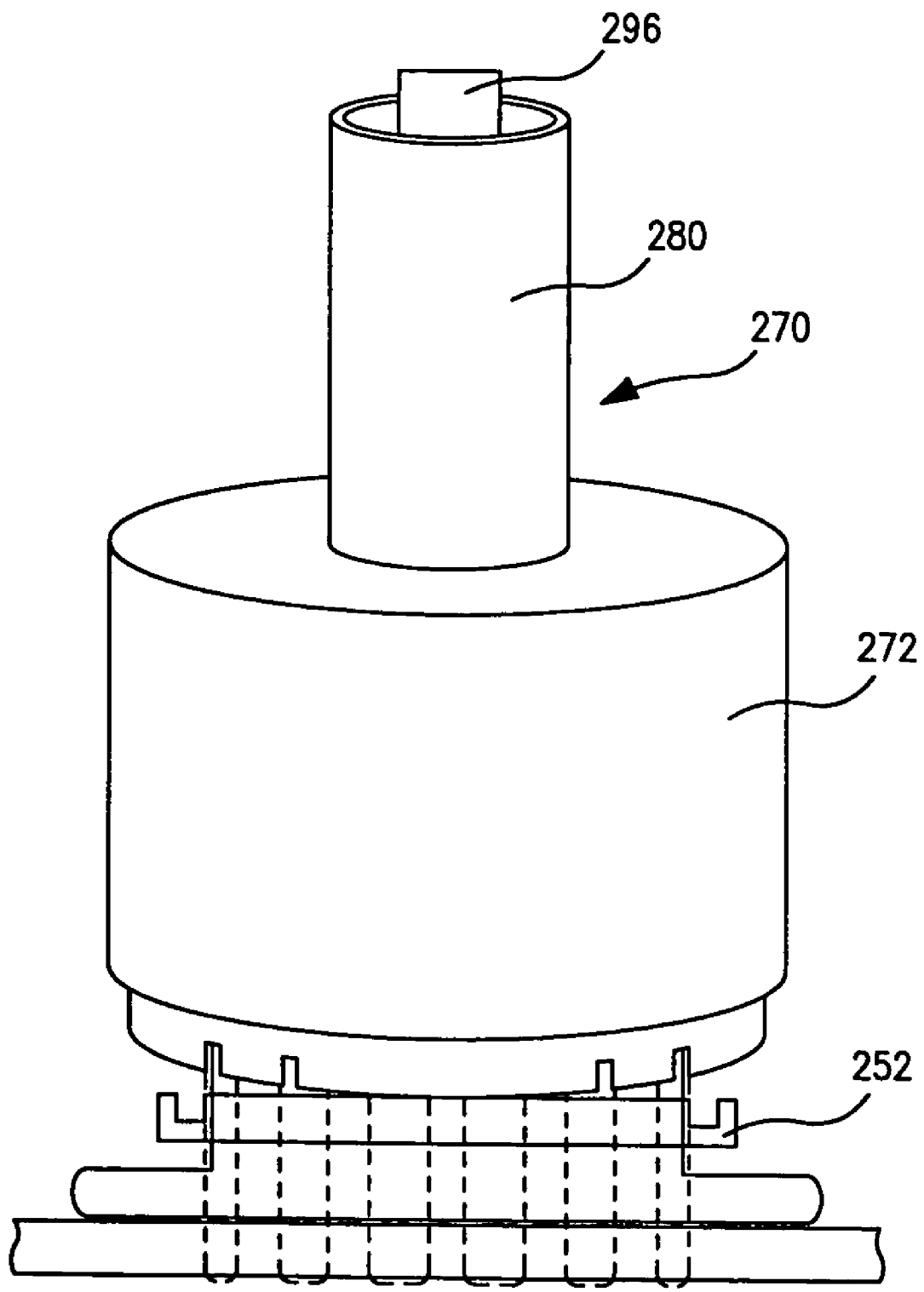

The process for pressing the band 220 onto the frame portion 252 can be facilitated by using a suture tensioning tool 290 as set forth in FIGS. 30a-b and 31. The suture tensioning tool 290 is mounted to the handle 296 for the valve holder 298. The suture tensioning tool 290 includes notches 292 or other suture tensioning devices around its circumference. In operation, the valve 250 is secured by a plurality of sutures 260 to a prepared valvar rim 262 by bringing the sutures through a suture ring 264, through a portion of the valvar rim 262 and returning the suture through the suture ring 264. The ends of the sutures 260 extending away from the valvar rim 262 are drawn up to the suture tensioning tool 290 and are retained thereto in the notches 292. After each of the sutures 260 is secured in position on the suture retaining tool, with any slack in the sutures 260 removed, the band 220 and pressing tool 270 are advanced over the handle 296, suture tensioning tool 290 and valve 250. With the handle 296 of the valve holder 298 and the handle of the pressing tool held stationary in one hand of the surgeon, the surgeon turns the body 272 until the band 220 locks onto the frame portion 252. The tools 270, 290 can then be removed and any excess material can then be removed from the ends of the sutures 260.

All patents and publications referenced herein are hereby incorporated by reference in their entireties.

Although particular embodiments of the invention have been described herein in some detail, this has been done for the purpose of providing a written description of the invention in an enabling manner and to form a basis for establishing equivalents to structure and method steps not specifically described or listed. It is contemplated by the inventors that the scope of the limitations of the following claims encompasses the described embodiments and equivalents thereto, including monitors, now known and coming into existence during the term of the patent. Thus, it is expected that various changes, alterations, or modifications may be made to the invention as described herein without departing from the spirit and scope of the invention as defined by the appended claims.

The invention claimed is:

1. A heart valve prosthesis comprising:
an annular valve body comprising a frame and a suturing ring, the frame including at least one outwardly extending annular flange adjacent to the suturing ring;
a band comprising at least one inwardly extending annular flange that is capable of engagement with the annular flange of the frame such that a tortuous path is formed between the annular flange of the frame and the annular flange of the band that can engage and restrain a suture placed therein;
at least one split portion on the band adapted to lock the band in engagement with the flange of the frame;
wherein the split portion includes two split ends defining a split extending through a radial width of the band;
wherein the split ends are spreadable relative to one another and are secured by a restraint mechanism; and
wherein the restraint mechanism includes a suture.

2. The heart valve prosthesis of claim 1 wherein the band includes a plurality of splits that extend partially through the band.

3. The heart valve prosthesis of claim 1 wherein the prosthesis is a mechanical valve.

4. A heart valve prosthesis comprising:
an annular valve body comprising a frame and a suturing ring, the frame forming a central passage defining a longitudinal axis and including at least one outwardly extending annular flange longitudinally spaced from to the suturing ring relative to the longitudinal axis;
a band comprising at least one inwardly extending annular flange that is capable of engagement with the annular flange of the frame such that a tortuous path is formed between the annular flange of the frame and the annular flange of the band that can engage and restrain a suture placed therein;
at least one split portion on the band adapted to lock the band in engagement with the flange of the frame;
wherein the band includes a plurality of splits that extend partially through the band; and
wherein the plurality of splits define at least one locking tab on the band.

5. The heart valve prosthesis of claim 4 wherein the band includes at least two locking tabs.

6. The heart valve prosthesis of claim 4 wherein the locking tab includes at least one barbed portion.

7. The heart valve prosthesis of claim 6 wherein the barbed portion is capable of engaging a portion of the flange of the frame on an inflow portion of the flange.

8. The heart valve prosthesis of claim 4, wherein the annular valve body extends between a suture ring side and a second side opposite the suture ring side, and further wherein the suturing ring is provided at the suture ring side and the annular flange of the frame is located longitudinally between the suturing ring and the second side.

9. A heart valve prosthesis comprising:
an annular valve body comprising a frame and a suturing ring, the frame including at least one outwardly extending annular flange adjacent to the suturing ring, the annular flange having at least one recess formed on an upper, outflow side of the flange;
a band comprising at least one inwardly extending annular flange that is capable of engagement with the annular flange of the frame, including a portion of the flange of the band capable of engagement with the at least one recess formed on the annular flange of the frame, such that a tortuous path is formed between the annular flange of the frame and the annular flange of the band that can engage and restrain a suture placed therein; and
at least one locking element on one of the band or the flange of the frame adapted to lock the band in engagement with the flange of the frame upon insertion of the locking element into a complimentary structure provided with an other of the band or the flange of the frame, wherein the locking element includes at least one locking tab.

10. The heart valve prosthesis of claim 9 wherein the prosthesis is a tissue valve.

11. The heart valve prosthesis of claim 9 wherein the frame is a stent.

12. The heart valve prosthesis of claim 9 wherein the locking tab is on the band.

13. The heart valve prosthesis of claim 9 wherein the locking tab is on a flange of the frame.

14. The heart valve prosthesis of claim 9 wherein the locking element includes at least two locking tabs.

15. The heart valve prosthesis of claim 9 wherein the locking tab includes at least one barbed portion.

16. The heart valve prosthesis of claim 15 wherein the barbed portion is capable of engaging a portion of the flange of the frame on an inflow portion of the flange.

17. The heart valve prosthesis of claim 9 wherein the prosthesis is a mechanical valve.

18. The heart valve prosthesis of claim 9, wherein the annular flange of the frame is longitudinally spaced from the suturing ring.

19. A heart valve prosthesis comprising:
an annular valve body comprising a frame and a suturing ring, the frame including at least one outwardly extending annular flange adjacent to the suturing ring;
a band comprising at least one inwardly extending annular flange that is capable of engagement with the annular flange of the frame, including a portion of the flange capable of engagement with a portion of the annular flange of the frame, such that a tortuous path is formed between the annular flange of the frame and the annular flange of the band that can engage and restrain a suture placed therein;
at least one locking tab formed by one of the band or the flange of the frame adapted to lock the band in engagement with the flange of the frame; and
wherein the prosthesis includes at least two locking tabs.

20. A heart valve prosthesis comprising:
an annular valve body comprising a frame and a suturing ring, the frame including at least one outwardly extending annular flange adjacent to the suturing ring;
a band comprising at least one inwardly extending annular flange that is capable of engagement with the annular flange of the frame, including a portion of the flange capable of engagement with a portion of the annular flange of the frame, such that a tortuous path is formed between the annular flange of the frame and the annular flange of the band that can engage and restrain a suture placed therein;
at least one locking tab on one of the band or the flange of the frame adapted to lock the band in engagement with the flange of the frame; and
wherein the locking tab includes at least one barbed portion extending from a tab portion, the barbed portion having a flat surface having a longitudinal axis projecting perpendicular to the tab portion.

21. The heart valve prosthesis of claim 20 wherein the barbed portion is capable of engaging a portion of the flange of the frame on an inflow portion of the flange.

22. A heart valve prosthesis comprising:
an annular valve body comprising a frame and a suturing ring, the frame including at least one outwardly extending annular flange adjacent to the suturing ring;
a band comprising an outside portion and at least one inwardly extending annular flange that define a recess within which the annular flange of the frame is nested upon final assembly, including a portion of the flange capable of engagement with a portion of the annular flange of the frame, such that a tortuous path is formed between the annular flange of the frame and the annular flange of the band that can engage and restrain a suture placed therein;
at least one locking tab on one of the band or the flange of the frame adapted to lock the band in engagement with the flange of the frame; and
wherein the prosthesis is a mechanical valve.

* * * * *